US010642957B1

United States Patent
Pinsonneault et al.

(10) Patent No.: US 10,642,957 B1
(45) Date of Patent: May 5, 2020

(54) SYSTEMS AND METHODS FOR DETERMINING, COLLECTING, AND CONFIGURING PATIENT INTERVENTION SCREENING INFORMATION FROM A PHARMACY

(71) Applicant: McKesson Corporation, Irving, TX (US)

(72) Inventors: Roger G. Pinsonneault, Alpharetta, GA (US); Kristina Crockett, Atlanta, GA (US)

(73) Assignee: MCKESSON CORPORATION, Irving, TX (US)

(*) Notice: Subject to any disclaimer, the term of this patent is extended or adjusted under 35 U.S.C. 154(b) by 618 days.

(21) Appl. No.: 14/519,626

(22) Filed: Oct. 21, 2014

(51) Int. Cl.
*G06F 19/00* (2018.01)
(52) U.S. Cl.
CPC .................. *G06F 19/328* (2013.01)
(58) Field of Classification Search
CPC ..... G06F 19/328; G06F 19/465; G06Q 50/24; G06Q 10/087; G16H 10/60; G16H 10/65; G16H 40/20; G16H 10/40; G16H 10/20; G16H 40/63
USPC .............................................................. 705/2
See application file for complete search history.

(56) References Cited

U.S. PATENT DOCUMENTS

| | | |
|---|---|---|
| 5,235,702 A | 8/1993 | Miller |
| 5,244,556 A | 9/1993 | Inoue |
| 5,359,509 A | 10/1994 | Little et al. |
| 5,544,044 A | 8/1996 | Leatherman |
| 5,550,734 A | 8/1996 | Tarter et al. |
| 5,578,003 A | 11/1996 | Borger |
| 5,628,530 A | 5/1997 | Thornton |

(Continued)

FOREIGN PATENT DOCUMENTS

| | | |
|---|---|---|
| CA | 2482370 A1 | 3/2006 |
| WO | 1995003569 A3 | 2/1995 |

(Continued)

OTHER PUBLICATIONS

Sampson, R.J., Taking Control of Health Care Costs, Best's Review—Life Health Insurance Edition, Nov. 1983, vol. 84, Issue 7, USA; Abstract only.

(Continued)

*Primary Examiner* — Hiep V Nguyen
(74) *Attorney, Agent, or Firm* — Alston & Bird LLP

(57) ABSTRACT

A healthcare claim transaction may be received by a service provider computer from a pharmacy computer. An intervention service for a patient may be identified and the screening parameters to be obtained from the patient for the intervention service may be identified. The service provider computer may generate a reject response and insert a reject code and/or message notifying the pharmacy of the first screening parameter to obtain from the patient. The rejection response may be sent to the pharmacy computer, which may subsequently send a resubmitted healthcare claim transaction that includes the requested first screening parameter data for the patient. The service provider computer may parse the transaction to identify the data. The iterative process may continue until all of the screening parameter data for the patient is received by the service provider computer, which may transmit that data to a claims processor computer.

20 Claims, 6 Drawing Sheets

(56) References Cited

U.S. PATENT DOCUMENTS

| | | |
|---|---|---|
| 5,644,778 A | 7/1997 | Burks et al. |
| 5,704,044 A | 12/1997 | Tarter et al. |
| 5,832,447 A | 11/1998 | Rieker et al. |
| 5,950,169 A | 9/1999 | Borghesi et al. |
| 6,006,242 A | 12/1999 | Poole et al. |
| 6,012,035 A | 1/2000 | Freeman et al. |
| 6,073,104 A | 6/2000 | Field |
| 6,081,786 A | 6/2000 | Barry et al. |
| 6,202,923 B1 | 3/2001 | Boyer et al. |
| 6,208,973 B1 | 3/2001 | Boyer et al. |
| 6,324,516 B1 | 11/2001 | Shults et al. |
| 6,330,546 B1 | 12/2001 | Gopinathan et al. |
| 6,341,265 B1 | 1/2002 | Provost et al. |
| 6,343,271 B1 | 1/2002 | Peterson et al. |
| 6,578,003 B1 | 6/2003 | Camarda et al. |
| 6,632,251 B1 | 10/2003 | Ruffen et al. |
| 6,650,964 B2 | 11/2003 | Spano et al. |
| 6,671,692 B1 | 12/2003 | Marpe et al. |
| 6,671,693 B1 | 12/2003 | Marpe et al. |
| 6,714,918 B2 | 3/2004 | Hillmer et al. |
| 6,757,898 B1 | 6/2004 | Ilsen et al. |
| 6,769,228 B1 | 8/2004 | Mahar |
| 7,155,397 B2 | 12/2006 | Alexander et al. |
| 7,720,697 B1 | 5/2010 | Silverstein |
| 8,036,913 B1 | 10/2011 | Pinsonneault et al. |
| 8,046,242 B1 | 10/2011 | daCosta |
| 8,060,379 B1 | 11/2011 | Pinsonneault et al. |
| 8,099,339 B1 | 1/2012 | Pinsonneault |
| 8,244,556 B1 | 8/2012 | Ringold |
| 8,335,672 B1 | 12/2012 | Ringold |
| 8,386,274 B1 | 2/2013 | Pinsonneault |
| 8,386,276 B1 | 2/2013 | Liu et al. |
| 8,392,209 B1 | 3/2013 | Bertha et al. |
| 8,392,219 B1 | 3/2013 | Pinsonneault et al. |
| 8,688,468 B1 | 4/2014 | daCosta et al. |
| 8,725,532 B1 | 5/2014 | Ringold |
| 8,768,724 B2 | 7/2014 | Whiddon et al. |
| 9,122,783 B2 | 9/2015 | Carson et al. |
| 9,443,370 B2 | 9/2016 | Carson et al. |
| 2001/0041993 A1 | 11/2001 | Campbell |
| 2001/0047281 A1 | 11/2001 | Keresman |
| 2002/0002495 A1 | 1/2002 | Ullman |
| 2002/0029157 A1 | 3/2002 | Marchosky |
| 2002/0035488 A1 | 3/2002 | Aquila et al. |
| 2002/0046169 A1 | 4/2002 | Keresman et al. |
| 2002/0049617 A1 | 4/2002 | Lencki et al. |
| 2002/0055856 A1 | 5/2002 | Adams |
| 2002/0065687 A1 | 5/2002 | Onoue |
| 2002/0087583 A1 | 7/2002 | Morgan et al. |
| 2002/0111832 A1 | 8/2002 | Judge |
| 2002/0120559 A1 | 8/2002 | O'Mara et al. |
| 2002/0133503 A1 | 9/2002 | Amar et al. |
| 2002/0138155 A1 | 9/2002 | Bristol |
| 2002/0143434 A1 | 10/2002 | Greeven et al. |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0050803 A1 | 3/2003 | Marchosky |
| 2003/0069020 A1 | 4/2003 | Hillmer et al. |
| 2003/0074225 A1 | 4/2003 | Borsand et al. |
| 2003/0083903 A1 | 5/2003 | Myers |
| 2003/0120588 A1 | 6/2003 | Dodd et al. |
| 2003/0130868 A1 | 7/2003 | Coelho |
| 2003/0149625 A1 | 8/2003 | Leonardi et al. |
| 2003/0154163 A1 | 8/2003 | Phillips et al. |
| 2003/0158755 A1 | 8/2003 | Neuman |
| 2003/0229519 A1 | 12/2003 | Eidex et al. |
| 2003/0229540 A1 | 12/2003 | Algiene |
| 2004/0006490 A1 | 1/2004 | Gingrich et al. |
| 2004/0039599 A1 | 2/2004 | Fralic |
| 2004/0054685 A1 | 3/2004 | Rahn et al. |
| 2004/0064215 A1 | 4/2004 | Greeven et al. |
| 2004/0073457 A1 | 4/2004 | Kalies |
| 2004/0078234 A1 | 4/2004 | Tallal, Jr. |
| 2004/0078247 A1* | 4/2004 | Rowe, III .............. G06F 19/328 705/4 |
| 2004/0088187 A1 | 5/2004 | Chudy et al. |
| 2004/0093242 A1 | 5/2004 | Cadigan et al. |
| 2004/0117205 A1 | 6/2004 | Reardan et al. |
| 2004/0117323 A1 | 6/2004 | Mindala |
| 2004/0133452 A1* | 7/2004 | Denny, Jr. ............ G06F 19/328 705/2 |
| 2004/0148198 A1 | 7/2004 | Kalies |
| 2004/0178112 A1 | 9/2004 | Snyder |
| 2004/0225528 A1 | 11/2004 | Brock |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0065821 A1 | 3/2005 | Kalies |
| 2005/0090425 A1 | 4/2005 | Reardan et al. |
| 2005/0102169 A1 | 5/2005 | Wilson |
| 2005/0137912 A1 | 6/2005 | Rao et al. |
| 2005/0154627 A1 | 7/2005 | Zuzek et al. |
| 2005/0187791 A1 | 8/2005 | DiMaggio et al. |
| 2005/0187793 A1 | 8/2005 | Myles |
| 2005/0197862 A1 | 9/2005 | Paterson et al. |
| 2005/0209879 A1 | 9/2005 | Chalmers |
| 2005/0240473 A1 | 10/2005 | Ayers, Jr. et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0062734 A1 | 3/2006 | Melker et al. |
| 2006/0074717 A1 | 4/2006 | Feldman et al. |
| 2006/0106648 A1 | 5/2006 | Esharn et al. |
| 2006/0129434 A1 | 6/2006 | Smitherman et al. |
| 2006/0149784 A1 | 7/2006 | Tholl et al. |
| 2006/0184391 A1 | 8/2006 | Barre et al. |
| 2006/0217824 A1 | 9/2006 | Allmon |
| 2006/0259363 A1 | 11/2006 | Jhetam et al. |
| 2006/0266826 A1 | 11/2006 | Banfield et al. |
| 2007/0005402 A1 | 1/2007 | Kennedy et al. |
| 2007/0050209 A1 | 3/2007 | Yered |
| 2007/0050219 A1 | 3/2007 | Sohr |
| 2007/0136100 A1 | 6/2007 | Daugherty et al. |
| 2007/0162303 A1 | 7/2007 | Wiley et al. |
| 2007/0214009 A1 | 9/2007 | Epstein et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0260491 A1 | 11/2007 | Palmer et al. |
| 2007/0276697 A1 | 11/2007 | Wiley, II et al. |
| 2008/0015893 A1 | 1/2008 | Miller et al. |
| 2008/0015894 A1 | 1/2008 | Miller et al. |
| 2008/0097784 A1* | 4/2008 | Miller ................. G06Q 10/10 705/2 |
| 2008/0112615 A1 | 5/2008 | Obrea |
| 2008/0288281 A1 | 11/2008 | Shell et al. |
| 2008/0312954 A1 | 12/2008 | Ullrich et al. |
| 2009/0048863 A1 | 2/2009 | Kozlowski et al. |
| 2009/0144087 A1 | 6/2009 | Kelsch et al. |
| 2009/0164376 A1 | 6/2009 | Guthrie |
| 2009/0281824 A1 | 11/2009 | Hardaway |
| 2009/0327163 A1 | 12/2009 | Cullen et al. |
| 2010/0082367 A1 | 4/2010 | Hains et al. |
| 2010/0305975 A1* | 12/2010 | Daya .................... G06F 19/325 705/3 |
| 2010/0312576 A1 | 12/2010 | Brown et al. |
| 2010/0324936 A1 | 12/2010 | Vishnubhatla et al. |
| 2011/0106556 A1 | 5/2011 | Patel et al. |
| 2011/0145018 A1 | 6/2011 | Fotsch et al. |
| 2011/0161109 A1 | 6/2011 | Pinsonneault et al. |
| 2011/0173020 A1 | 7/2011 | Bailey et al. |
| 2011/0282690 A1 | 11/2011 | Patel et al. |
| 2011/0288886 A1 | 11/2011 | Whiddon et al. |
| 2012/0046970 A1 | 2/2012 | Potts et al. |
| 2012/0173263 A1 | 7/2012 | Nease et al. |
| 2012/0310661 A1* | 12/2012 | Greene ................ G06Q 10/087 705/2 |
| 2013/0151373 A1 | 6/2013 | Flanagan et al. |
| 2013/0253700 A1 | 9/2013 | Carson et al. |
| 2014/0025545 A1 | 1/2014 | Carson et al. |
| 2014/0156298 A1 | 6/2014 | Crawford et al. |

(56) References Cited

U.S. PATENT DOCUMENTS

| | | | |
|---|---|---|---|
| 2014/0188498 A1 | 7/2014 | Petrimoulx et al. | |
| 2017/0287061 A1 | 10/2017 | Chae et al. | |
| 2018/0012244 A1 | 1/2018 | Leonardi | |

FOREIGN PATENT DOCUMENTS

| | | |
|---|---|---|
| WO | 2000039737 A1 | 7/2000 |
| WO | 2007025295 A2 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, vol. 63, Issue 1, USA; Abstract only.

Anonymous, TechRx Announces Successful Beta Deployment of T-Rex. PR Newswire. May 13, 2002.

Final Office Action for U.S. Appl. No. 10/439,423 dated Dec. 24, 2009.

Final Office Action for U.S. Appl. No. 10/439,423 dated Dec. 9, 2008.

Final Office Action for U.S. Appl. No. 11/961,559 dated Nov. 10, 2010.

Final Office Action for U.S. Appl. No. 12/411,043 dated Jul. 7, 2011.

Final Office Action for U.S. Appl. No. 12/411,075 dated Oct. 26, 2011.

Final Office Action for U.S. Appl. No. 12/480,907 dated Apr. 2, 2013.

Final Office Action for U.S. Appl. No. 12/480,907 dated May 4, 2012.

Final Office Action for U.S. Appl. No. 12/730,897 dated Nov. 22, 2013.

Final Office Action for U.S. Appl. No. 12/820,750 dated Jul. 6, 2012.

Final Office Action for U.S. Appl. No. 13/566,693 dated Dec. 23, 2015.

Final Office Action for U.S. Appl. No. 13/566,693 dated Nov. 6, 2014.

Final Office Action for U.S. Appl. No. 13/628,623 dated Jun. 14, 2016.

Final Office Action for U.S. Appl. No. 13/628,623 dated Mar. 11, 2015.

Final Office Action for U.S. Appl. No. 13/735,212 dated Jun. 12, 2015.

Final Office Action for U.S. Appl. No. 13/763,618 dated Apr. 28, 2017.

Final Office Action for U.S. Appl. No. 13/763,618 dated Mar. 28, 2016.

Final Office Action for U.S. Appl. No. 13/927,862 dated Sep. 22, 2016, 17 pages.

Final Office Action for U.S. Appl. No. 131628,623 dated Jun. 14, 2016.

Final Office Action for U.S. Appl. No. 14/062,593 dated Nov. 4, 2016, 21 pages.

Final Office Action for U.S. Appl. No. 14/209,248 dated Nov. 4, 2016, 35 pages.

GAO publication GA0-01-662 "Medicaid: State Efforts to Control Improper Payments Vary" Jun. 2001.

Glaser, M. Computer Eliminates Third-Party Administrator. Drug Topics, Oradell: May 3, 1993. vol. 137, Issu.9: p. 54, 3 pgs. [Retr. From Internet Apr. 11, 2007], URL: <http://proquest.umi.com/pqdweb?did=779533&sid=5&Fmt=11&clientId=19649&RQT=309&VNam=PQD>.

Gregory J. Borca, "Technology Curtails Health Care Fraud" Managed Care Magazine, Apr. 2001.

HealthWatch Technology—HWT Inc. Website obtained from Mar. 25, 2002 web.archive.org.

International Search Report for PCT/US2003/015982 dated Jun. 2, 2004.

International Search Report for PCT/US2003/015992 dated Jun. 2, 2004.

Letter Restarting Period for Response for U.S. Appl. No. 13/566,693 dated Jul. 9, 2014.

McKesson & American Pharmacy Alliance Agree to Offer Omnlink Connectivity to Retail Pharmacies: More than 11,000 Pharmacies Gain Ability to Access Centralized Pharmacy Application. Bus. Wire. New York: Jul. 28, 1998 did=323992868&sid=4&Fmt=3&clientId=19649&RQT&VNam=PQD>.

NDC Code Direcotry Tool—https://web.archive.org/web/20090327121011/http://www.accessdata.fda.gov/scripts/cder/ndc/default.cfm dated Mar. 29, 2009.

NDC Code Directory Description—https://web_archive.org/web/20090603081835/http://www.fda.gov/Drugs/InformationOnDrugs/ucm142438.htm Jun. 3, 2009.

NDC Health Information Services Announces Contract with Arrow Pharmacy and Nutrition Centers for Pre & Post Editing Service. PR Newswire. New York: Mar. 11, 1999. p. 1. [Retr. Internet Oct. 30, 2007] URL: <http://proquest.umi.com/pqdweb?did=39644468&sid=4&Fmt=3&clientId=19649&RQT=309&VNam=PQD>.

NDC Health Provides United Drugs With Intelligent Valued-Added Network Services and New Information Solutions. PR Newswire. New York: Dec. 12, 2000. p. 1. [Retr. Internet 04/11107] URL: <http://proquest.umi.com/pqdweb?did=65133864&sid=4&Fmt=3&clientId=19649&RQT=309&VNam=PQD>.

Non-final Office Action for U.S. Appl. No. 10/439,423 dated Apr. 28, 2009.

Non-final Office Action for U.S. Appl. No. 10/439,423 dated Jul. 31, 2008.

Non-final Office Action for U.S. Appl. No. 11/961,559 dated Mar. 3, 2010.

Non-final Office Action for U.S. Appl. No. 12/411,043 dated Feb. 8, 2011.

Non-final Office Action for U.S. Appl. No. 12/411,075 dated Jul. 7, 2011.

Non-Final Office Action for U.S. Appl. No. 12/411,075 dated May 22, 2013.

Non-Final Office Action for U.S. Appl. No. 12/480,907 dated Sep. 20, 2011.

Non-Final Office Action for U.S. Appl. No. 12/730,897 dated Nov. 8, 2012.

Non-Final Office Action for U.S. Appl. No. 12/730,897 dated Sep. 29, 2011.

Non-Final Office Action for U.S. Appl. No. 12/820,750 dated Feb. 1, 2012.

Non-Final Office Action for U.S. Appl. No. 121480,907 dated Sep. 12, 2012.

Non-Final Office Action for U.S. Appl. No. 13/566,693 dated Apr. 30, 2014.

Non-final Office Action for U.S. Appl. No. 13/566,693 dated Jul. 23, 2015.

Non-final Office Action for U.S. Appl. No. 13/628,623 dated Dec. 18, 2015.

Non-Final Office Action for U.S. Appl. No. 13/628,623 dated Sep. 25, 2014.

Non-Final Office Action for U.S. Appl. No. 13/735,212 dated Jan. 14, 2015.

Non-final Office Action for U.S. Appl. No. 13/763,618 dated Sep. 22, 2015.

(56) References Cited

OTHER PUBLICATIONS

Non-Final Office Action for U.S. Appl. No. 13/763,618 dated Sep. 23, 2016, 21 pages.
Non-final Office Action for U.S. Appl. No. 13/927,862 dated Jul. 6, 2015.
Non-Final Office Action for U.S. Appl. No. 14/062,593 dated Jun. 3, 2016.
Non-final Office Action for U.S. Appl. No. 14/062,593 dated Sep. 2, 2015.
Non-Final Office Action for U.S. Appl. No. 14/209,248 dated Apr. 22, 2016.
Non-Final Office Action for U.S. Appl. No. 131763,618 dated Jan. 15, 2015.
Notice of Allowance for U.S. Appl. No. 13/538,377 dated Dec. 27, 2013.
NPPES Registry Lookup Tool—https://web.archive.org/web/20130213231441/https://npiregistry.cms.hhs.gov/NPPESRegistry/NIPRegistryHome.do dated Feb. 13, 2013.
Office Action for Canadian Application No. 2,485,031 dated Apr. 5, 2012.
Office Action for Canadian Application No. 2,485,034 dated Nov. 22, 2011.
Office Action for U.S. Appl. No. 14/062,593 dated Jun. 3, 2016.
Office Action for U.S. Appl. No. 14/062,593 dated May 18, 2018.
Office Action for U.S. Appl. No. 14/062,593 dated Nov. 4, 2016.
Office Action for U.S. Appl. No. 14/062,593 dated Sep. 2, 2015.
Office Action for U.S. Appl. No. 14/062,593 dated Sep. 29, 2017.
Office Action for U.S. Appl. No. 14/209,248 dated Apr. 22, 2016.
Office Action for U.S. Appl. No. 14/209,248 dated Jan. 26, 2018.
Office Action for U.S. Appl. No. 14/209,248 dated Jul. 13, 2017.
Office Action for U.S. Appl. No. 14/209,248 dated May 5, 2018.
Office Action for U.S. Appl. No. 14/209,248 dated Nov. 4, 2016.
Office Action for U.S. Appl. No. 14/209,248 dated Oct. 5, 2018.
Pharmacy Industry Leaders Launch Firm to Supply Real-Time Data. PR Newswire. New York: Jul. 30, 2001. p. 1. [Retr. Internet 10130/07] URL: <http://proquest.umi.com/pqdweb?did=77135077&sid=4&Fmt=11&clientId=19649&RQT=309&VNarTFPQD>.
Radcliffe, J.G.Y., The Insurance Industry's Use of Databases to Prevent and Detect Fraud, and Improve.
Recoveries, European Convention on Security and Detection, Conference Publication No. 408, May 16-18, 1995, pp. 216-224.
Stefano, Bordoni. InsuranceFraudEvaluation A Fuzzy Expert System, 2001 IEEE International Fuzzy Systems Conference, pp. 1491-1494.
Sternberg et al., Using Cultural Algorithyms too Support Re-engineering of Rule-Based Expert systems in Dynamic Performance Environments: A Case Study in Fraud Detection, IEEE Transactions on Evolutionary Computation, vol. 1 No. 4, Nov. 1997, pp. 225-243.
Titus, Nancy Riaden. Health Insurance Industry Battles High Cost Fraud, Journal Record, Nov. 20, 1993, pg. no cite.
Wholesalers Get Into Technology Game. Chain Drug Review. Feb. 15, 1999. p Rx20 [Retr. From Internet Oct. 30, 2007] URL:<http://www.accessmylibrary.com/coms/summary_0286-487914_ITM>.
Office Action for U.S. Appl. No. 14/062,593 dated Jun. 6, 2019.
Office Action for U.S. Appl. No. 14/062,593 dated Oct. 4, 2019.
"Informatics and Clinical Decision Support", [online] retrieved from the Wayback machine: <https://web.archive.org/web/20170302011019/http://www.medscape.org:80/viewarticle/571099> dated (Mar. 2, 2017).
"NCPDP Recommendations for Improving Prescription Drug Monitoring Programs", National Council for Prescription Drugs Program, White Paper, dated May 2015, pp. 1-28.
"Prescription Drug Monitoring Frequently Asked Questions (FAQ)" [online], retrieved from the Internet: <http://www.pdmpassist.org/content/prescription-drug-monitoring-frequently-asked-questions-faq>.
"State Prescription Drug Monitoring Programs" [online], retrieved from the Internet: <https://www.deadiversion.usdoj.gov/faq/rx_monitor.htm> [retrieved Jun. 2016].
"The Alliance of States with Prescription Monitoring Programs" [online], retrieved from the Internet: <http://dhhs.ne.gov/DOP%20document%20library/Alliannce%20of%20States%20with%20Presscription&20Monitoring%20Programs.pdf> (2012).
Simeone, R et al. "An Evaluation of Prescription Drug Monitoring Programs" dated Sep. 1, 2006.

* cited by examiner

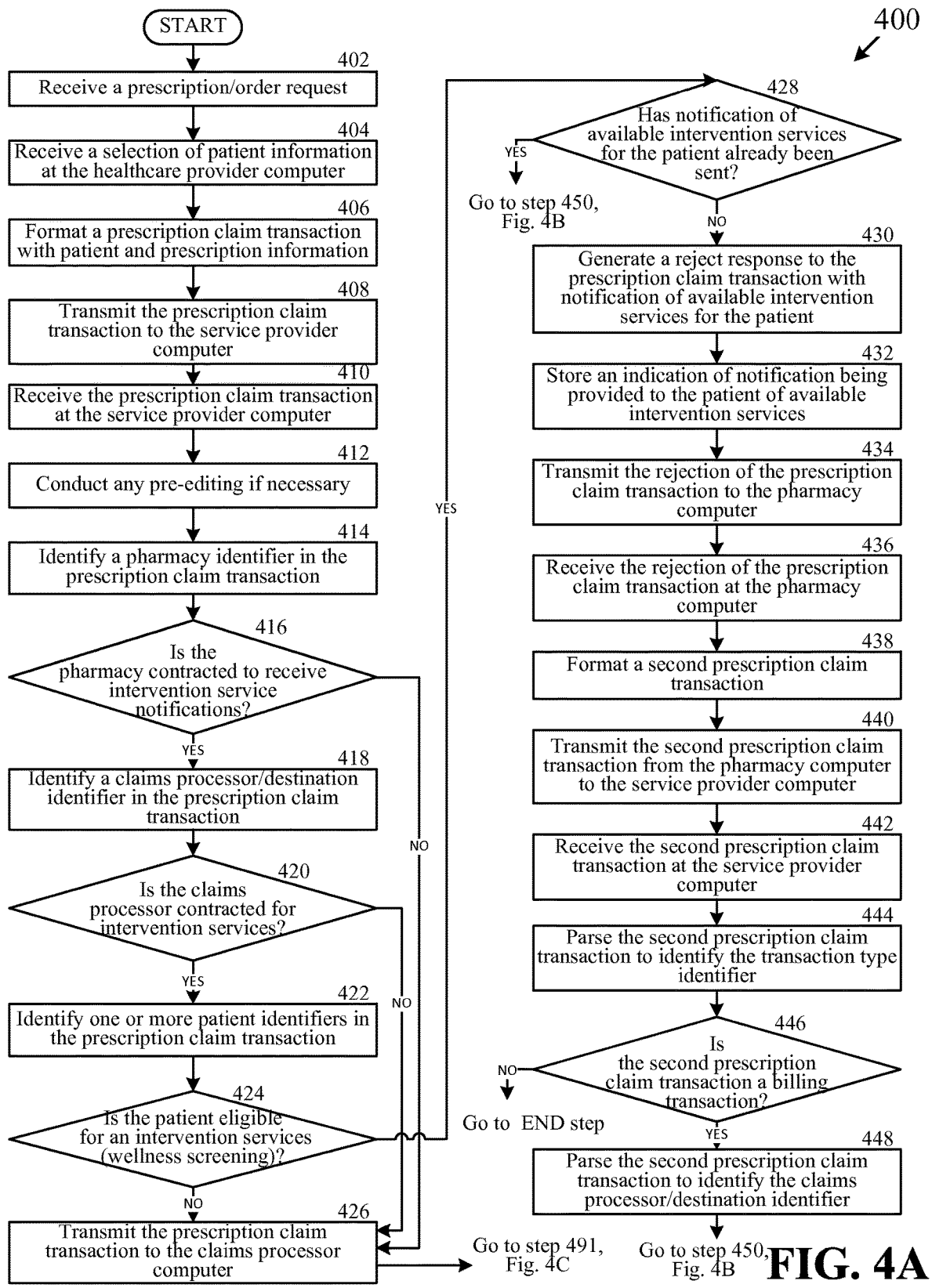

SYSTEMS AND METHODS FOR DETERMINING, COLLECTING, AND CONFIGURING PATIENT INTERVENTION SCREENING INFORMATION FROM A PHARMACY

TECHNICAL FIELD

Aspects of the disclosure relate generally to healthcare transactions and more particularly to systems and methods for determining, collecting, configuring, and transmitting patient screening information received from a pharmacy during a patient intervention service.

BACKGROUND

An intervention service is an effort to promote behaviors that optimize mental and physical health of the patient or discourage or reframe behaviors of the patient considered potentially health-averse. Wellness screenings are one form of intervention service. In one example, wellness screening may be conducted by a pharmacist, another pharmacy employee, or other healthcare provider. In a wellness screening, certain vital statistics of a patient may be collected. In one example, those vital statistics may include blood pressure, total cholesterol measurement, high-density lipoproteins cholesterol measurement, low-density lipoproteins cholesterol measurement, triglycerides measurement, blood glucose measurement, patient height, patient weight, and patient waist measurement. Other statistics or information may also be collected from the patient in a wellness screening.

Other forms of intervention service include, but are not limited to, medication therapy management (MTM) services, immunization messaging, cash prescription monitoring, refill adherence, high-risk medication monitoring, and diabetic screenings or monitoring. High-risk medications are a listing of medications published by the Centers for Medicare and Medicaid Services (CMS) and identified as posing a higher risk to patients, especially to seniors. When one or more of the listed high-risk medications are prescribed to a patient or a predetermined number of refills for the particular high-risk medication has been reached or exceeded as part of the current healthcare claim transaction, it may be beneficial to notify the pharmacy to alert the pharmacy to the fact and to request verification that the one or additional high-risk medication should be requested for the patient identified in the healthcare claim transaction.

MTM services include five core components: a medication therapy review, personal medication record, medication-related action plan, intervention and/or referral, and documentation and follow-up. MTM services include medical care provided by pharmacists whose aim is to optimize drug therapy and improve therapeutic outcomes for patients. MTM services include a broad range of professional activities including, but not limited to, performing patient assessment and/or a comprehensive medication review, formulating a medication treatment plan, monitoring efficacy and safety of medication therapy, enhancing medication adherence through patient empowerment and education, documenting and communicating MTM services to prescribers in order to maintain comprehensive patient care.

A medication therapy review is a systematic process of collecting patient and medication-related information which occurs during the pharmacist-patient encounter. In addition, the medication therapy review assists in the identification and prioritization of medication-related problems. During the medication therapy management encounter, the pharmacist develops a personal medication record for use by the patient. The personal medication record includes all prescription and non-prescription products/medications and may need to be updated periodically. After assessing and identifying medication-related problems, the pharmacist develops a patient-specific medication-related action plan. The medication-related action plan is a list of self-management actions necessary to achieve the patient's specific health goals. In addition, the patient and pharmacist utilize the medication-related action plan to record actions and track progress towards health goals. During the medication therapy management session, the pharmacist identifies medication-related problems and determines appropriate interventions for resolution. Following the patient encounter and/or intervention, the pharmacist must document his/her encounter and determine appropriate patient follow-up. The other intervention services can have similar documentation requirements for the pharmacist.

One problem related to the pharmacies providing intervention services to patients and the collection of data (e.g., screening parameter data) from the patient at the pharmacy is knowing what information may need to be collected for a particular intervention service in order to satisfy a particular claims processor's requirements and for the pharmacy to receive payment for conducting the intervention service. Another problem can be getting the collected data to the claims processor who is sponsoring (e.g., paying for) these intervention services. While pharmacies, via their pharmacy practice management systems (e.g., the pharmacy computer) are accustomed to submitting prescription claim transactions for payment of prescription medications, products, and/or services by claims processors, those same pharmacy practice management systems are not capable of collecting and sending all the data that must be collected during an intervention service in a single transaction.

Further, another problem related to intervention services involves situations when the intervention service is not completed (in whole or in part) or certain screening parameter data that is to be obtained from a patient during an intervention service is not obtained. Currently, there is no method of requesting or obtaining from the pharmacy, such as via the pharmacy practice management system information as to why the intervention service was not completed or certain screening parameter data was not obtained. This situation leaves the claims processor or sponsor without the information from the intervention service and without any understanding of why the information could not be obtained.

BRIEF DESCRIPTION OF THE DRAWINGS

Reference will now be made to the accompanying drawings, which are not necessarily drawn to scale, and wherein:

FIGS. 4A-C illustrate a flow chart of an example method for method for determining, collecting, configuring, and transmitting information derived during an intervention services, such as a wellness screening, available for an eligible patient, according to one exemplary embodiment.

DETAILED DESCRIPTION OF EXEMPLARY EMBODIMENTS

Figure 1:
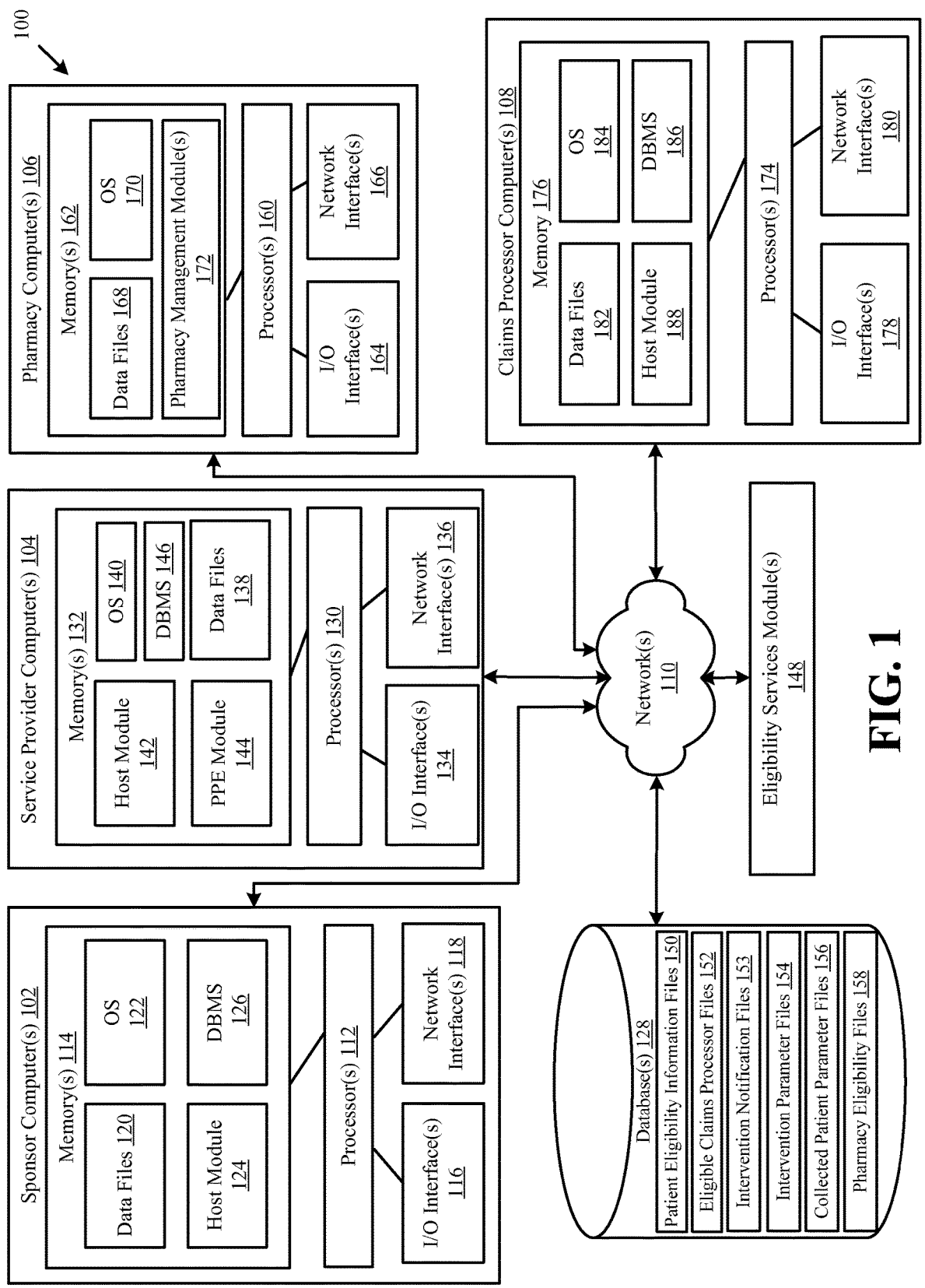
FIG. 1 illustrates an example system for facilitating, among other things, the determination, collection, configuration, and transmission of wellness screening requests and data and/or other patient intervention services associated with an intervention opportunity provided to a patient at a pharmacy, according to one exemplary embodiment.

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods for determining, collecting, configuring, and/or transmitting information derived associated with an intervention service at a pharmacy, such as a wellness screening or medication therapy management program that may be available for a patient. In this regard, the available intervention service may be determined as a part of the processing of a healthcare transaction, such as a predetermination of benefits transaction, healthcare claim transaction, prescription claim or billing request, healthcare order transaction, or e-prescription transaction (e.g., electronic prescription order transaction, e-script, or e-prescription).

In some example implementations, a prescription claim transaction may be communicated from a pharmacy computer to a service provider computer. In one example, the prescription claim transaction may be a National Council for Prescription Drug Programs (NCPDP) Telecommunication Standard formatted prescription claim transaction. The service provider computer can parse the prescription claim transaction to identify one or more pharmacy identifiers identifying the pharmacy from which the transaction was received, one or more destination identifiers (e.g., Banking Identification Number (BIN Number), BIN Number and Process Control Number (PCN) and/or BIN Number and Group ID) identifying the desired destination for the transaction (e.g., the claims processor, pharmacy benefits manager (PBM), Medicare payor, Medicaid payor, another governmental insurance payor, insurance provider/payor, etc.), and one or more identifiers for the patient. The service provider computer may then determine, based on the pharmacy identifier(s), whether the pharmacy is one that receives patient intervention services notifications by looking for matching pharmacy identifiers in a schedule or database of records for pharmacies who have requested or contracted to receive such notifications. The service provider computer may also determine, based on the destination identifier(s), whether the claims processor/PBM/insurance provider is one that has contracted for intervention services by looking for matching destination identifiers in a schedule or database of records for claims processors/PBMs/insurance providers who have contracted to such intervention services notifications to pharmacies and other healthcare providers. The service provider computer may also determine, based on the patient identifier(s), whether the patient is eligible for an intervention service (e.g., wellness screening, blood pressure monitoring, MTM services, immunization messaging, cash prescription monitoring, refill adherence, high-risk medication monitoring, and diabetic screening or monitoring, etc.) by looking for a matching patient identifier in a schedule or database or records identifying patients for which an intervention service, such as wellness screening, is available. In certain example embodiments, the available intervention service may be determined from patient eligibility information accessed from a patient eligibility file.

If a wellness screening, or other intervention service, is available for the patient and if the pharmacy and/or the claims processor has contracted for intervention services, then the service provider computer can generate a reject response to the prescription claim transaction. The service provider computer can insert in or otherwise provide an indication of the availability of an intervention service for the identified patient with the reject response and transmit the reject response back to the pharmacy computer from which the prescription claim transaction originated. In one example, the service provider computer may employ an eligibility services module to determine whether an intervention service (such as a wellness screening) is available for the patient identified in the prescription claim transaction. The eligibility services module may access a patient eligibility file to determine whether a patient intervention service is available for the patient and/or medication identified in the prescription claim transaction. Further, the eligibility services module may determine if a patient intervention service is available for the patient based on, the age of the patient, the sex of the patient, or the fill number (e.g., for high-risk medication monitoring) provided in the prescription claim transaction. The eligibility services module may determine whether an intervention services notification has previously been sent to the pharmacy computer, communicating availability of the intervention service for the identified patient. If an intervention services notification has not been previously communicated for the patient, the eligibility services module may generate an intervention services notification to be communicated to the pharmacy computer along with a reject response.

The service provider computer can then receive another prescription claim transaction from the pharmacy computer. The service provider computer can parse the second prescription claim transaction to determine the one or more destination identifiers, the one or more patient identifiers identifying the patient, and the one or more pharmacy identifiers identifying the pharmacy from which the second prescription claim transaction was received. The service provider computer may then determine, based on the destination identifier(s) if the second prescription claim transaction is for an intervention encounter for a patient by looking for matching destination identifiers in a schedule or database of records of destination identifiers identifying intervention encounters. The service provider computer may also determine, based on the pharmacy identifier(s), if the pharmacy provides intervention services and, based on the patient identifier(s), if the patient is eligible for an intervention service, such as wellness screening, in a manner similar to that described above.

Based on a determination that the destination identifier(s) identifies the second prescription claim transaction as an intervention encounter, such as a wellness screening for the patient, the service provider computer may determine that parameters that need to be collected, measured, tested for, asked of, etc. from the patient. If multiple parameters are to be collected, measured, tested for, and/or asked of the patient, the service provider computer may determine the first parameter (hereinafter referred to as a screening parameter). The service provider computer may identify a reject code identifying the first screening parameter and may generate a reject response to the second prescription claim transaction. The service provider computer can include the identified reject code and/or a message identifying the screening parameter to provide in the resubmission of the transaction. The service provider computer may then transmit the reject response, along with the reject code and/or reject message identifying the first screening parameter, to the pharmacy computer.

The service provider may then receive the resubmitted second prescription claim transaction from the pharmacy computer. The resubmitted transaction may include a first screening parameter in a previously agreed upon field of the resubmitted second prescription claim transaction. The service provider computer may parse the resubmitted transaction and determine if the requested screening parameter has been included in the resubmitted transaction. If the requested screening parameter has not been included, the service provider computer may determine if the resubmitted transaction includes a reason code identifying a reason why the resubmitted transaction does not include the requested screening parameter or when the information can be captured and reported and can store the reason code and/or the reason associated with the reason code in a database record associated with the one or more patient identifier(s) for the patient identified in the transaction. The service provider computer may then modify the resubmitted second prescription claim transaction by removing the reason code from the transaction and then transmit the transaction to the claims processor computer identified by the destination identifier in the resubmitted second prescription claim transaction.

If the resubmitted transaction includes the first screening parameter, the service provider computer may identify and store the screening parameter in a database record for the patient (such as by including in the record one or more of the patient identifiers). If additional screening parameters are needed from the patient, the service provider computer may again generate a reject response to the transaction and include in the reject response a reject code and/or message in one of the text fields of the reject response that identifies the next screening parameter to obtain. This can be done iteratively until all desired screening parameters for the particular intervention service have been received by the service provider computer from the pharmacy computer.

Once the service provider computer determines that all of the desired screening parameters have been received for the particular intervention service, the service provider computer may store an indication that the particular intervention service has been completed for the identified patient. The service provider computer may then generate an approval response to the resubmitted second prescription claim transaction (which may have been resubmitted several times depending on the number of screening parameters needed for the particular intervention service provided for the patient) and transmit the approval response to the pharmacy computer. The service provider computer may also transmit all of the screening parameters received for the patient during the intervention service to the claims processor computer identified in the destination identifier. For example, the service provider computer may transmit the patient identifier(s), an indication of the intervention service performed, and the screening parameters received from the pharmacy computer to the claims processor computer in a batch file, either alone or with information from other intervention services provided for other patients. In another example embodiment, the service provider computer may generate a single billing or service billing transaction (e.g., a prescription billing transaction) that includes the patient identifier(s) from the second prescription billing transaction, an indication (such as a code) of the intervention service provided to the patient, and all of the screening parameters (e.g., two or more screening parameters) received from the pharmacy computer for the patient while receiving the intervention service. The service provider computer may then transmit the single billing transaction to the claims processor computer identified by the destination identifier in the second prescription claim transaction.

System Overview

FIG. 1 illustrates an example system 100 for facilitating, among other things, the determination, collection, configuration, and transmission of wellness screening requests and data and/or other patient intervention services associated with an intervention opportunity provided to a patient at a pharmacy, according to one example embodiment of the disclosure. As shown in FIG. 1, the system 100 may include one or more eligibility sponsor computers 102, service provider computers 104, pharmacy computers 106, and/or claims processor computers 108. As desired, each of the eligibility sponsor computer 102, service provider computer 104, pharmacy computer 106, and/or claims processor computer 108 may include one or more processing devices that may be configured for accessing and reading associated computer-readable media having stored data thereon and/or computer-executable instructions for implementing various embodiments of the disclosure.

Generally, network devices and systems, including one or more eligibility sponsor computers 102, service provider computers 104, pharmacy computers 106, and/or claims processor computers 108, may include or otherwise be associated with suitable hardware and/or software for transmitting and receiving data and/or computer-executable instructions over one or more communication links or networks. These network devices and systems may also include any number of processors for processing data and executing computer-executable instructions, as well as other internal and peripheral components currently known in the art or which may be developed in the future. Further, these network devices and systems may include or be in communication with any number of suitable memory devices operable to store data and/or computer-executable instructions. By executing computer-executable instructions, each of the network devices may form a special-purpose computer or particular machine. As used herein, the term "computer-readable medium" describes any medium for storing computer-executable instructions.

As shown in FIG. 1, the one or more eligibility sponsor computers 102, service provider computers 104, pharmacy computers 106, and/or claims processor computers 108 may be in communication with each other via one or more networks, such as the network 110, which may include one or more independent and/or shared private and/or public networks including the Internet or a publicly switched telephone network. In other example embodiments, one or more components of the system 100 may communicate via direct connections and/or communication links. Each of these components—the eligibility sponsor computer 102, service provider computer 104, pharmacy computer 106, claims processor computer 108, and the network 110—will now be discussed in further detail. Although the components are generally discussed as singular components, as may be implemented in various example embodiments, in alternative exemplary embodiments each component may include any number of suitable computers and/or other components.

With continued reference to FIG. 1, one or more eligibility sponsor computers 102 may be associated (e.g., located within) with one or more organizations responsible for contracting an eligibility service program. For example, the sponsor may be an entity that provides information for intervention services that may be available for patients. The eligibility sponsor computer 102 may communicate information associated with intervention services available for eligible patients to the service provider computer 104 via, for example, the network 110. An eligibility sponsor computer 102 may be any suitable processor-driven device that facilitates the processing of the communicated information associated with intervention services, such as wellness screenings, MTM services, immunization messaging, cash prescription monitoring, refill adherence, high-risk medication monitoring, and diabetic screening or monitoring, etc, available for eligible patients to create, store, and maintain any data associated with the communication. The eligibility sponsor computer 102 may be a computing device that includes any number of server computers, mainframe computers, networked computers, desktop computers, personal computers, mobile devices, smartphones, digital assistants, personal digital assistants, tablet devices, Internet appliances, application-specific integrated circuits, microcontrollers, minicomputers, and/or any other processor-based devices. In certain example embodiments, the operations and/or control of the eligibility sponsor computer 102 may be distributed among several processing components. For example, the functionality associated with the eligibility sponsor computer 102 may be performed by one or more modules of the service provider computer 104 and/or the pharmacy computer 106.

In addition to including one or more processors 112, the eligibility sponsor computer 102 may further include one or more memory devices (or memory) 114, one or more input/output ("I/O") interfaces 116, and one or more network interfaces 118. The memory devices 114 may be any suitable memory devices, for example, caches, read-only memory devices, random access memory devices, magnetic storage devices, removable storage devices, etc. The memory devices 114 may store data, executable instructions, and/or various program modules utilized by the eligibility sponsor computer 102, for example, data files 120, an operating system ("OS") 122, a host module 124, and a database management system (DBMS) 126 to facilitate management of data files 120 and other data stored in the memory device 114 and/or one or more databases 128. The OS 122 may be a suitable software module that controls the general operation of the eligibility sponsor computer 102. The OS 122 may be any operating system known in the art or which may be developed in the future including, but not limited to, Microsoft Windows®, Apple OSX™ Apple iOS™, Google Android™, Linux, Unix, or a mainframe operating system.

The one or more I/O interfaces 116 may facilitate communication between the eligibility sponsor computers 102 and one or more input/output devices, for example, one or more user interface devices, such as a display, keypad, control panel, touch screen display, remote control, microphone, etc., that facilitate user interaction with the eligibility sponsor computers 102. For example, the one or more I/O interfaces 116 may facilitate entry of information associated with a patient by a sponsor employee. The one or more network interfaces 118 may facilitate connection of the eligibility sponsor computers 102 to one or more suitable networks, for example, the network 110 illustrated in FIG. 1. In this regard, the eligibility sponsor computers 102 may receive and/or communicate information to other network components of the system 100, such as the service provider computer 104.

With continued reference to FIG. 1, one or more service provider computers 104 may be associated with (e.g., located within or providing computing services for) a service provider or switch that can reside between and provide services for pharmacies and claims processors (e.g., PBMs, insurance providers, Medicare, Medicaid, etc.) in one example embodiment. In certain exemplary embodiments, the service provider computer 104 may be a switch/router that routes healthcare transactions and/or other healthcare requests between, for example, one or more pharmacy computers and one or more claims processor computers. For example, the service provider computer 104 may route healthcare transactions, such as a predetermination of benefits transaction, healthcare claim transaction, prescription claim transaction or billing request, healthcare order transaction, or e-prescription transaction (e.g., electronic prescription order transaction, e-script, or e-prescription), communicated from the pharmacy computer 106 to a claims processor computer 108, such as a PBM, a healthcare insurer, a Medicare payor, Medicaid payor, other governmental insurance payor, or other third-party insurance payor. The service provider computer 104 may include, but is not limited to, any suitable processor-driven device that is configured for receiving, processing, and fulfilling the healthcare transactions from the pharmacy computer 106 relating to prescription information including, but not limited to, medications, medication identifiers (e.g., medication name, National Drug Code (NDC code), RxNorm medication identifiers), quantity of medication to be dispensed, patient identifier information (i.e., patient first and last name, patient gender, patient date of birth, residence address of patient). Any number of eligibility sponsor computers 102, pharmacy computers 106, and/or claims processor computers 108 may be in communication with the service provider computer 104 as desired in various example embodiments.

The service provider computer 104 may include any number of special-purpose computers or other particular machines, application-specific integrated circuits, microcontrollers, personal computers, minicomputers, mainframe computers, servers, networked computers, and/or other processor-driven devices. In certain embodiments, the operations of the service provider computer 104 may be controlled by computer-executed or computer-implemented instructions that are executed by one or more processors of the service provider computer 104 to form a special-purpose computer or other particular machine that is operable to facilitate the receipt, routing, and/or processing of healthcare requests or healthcare transactions. The one or more processors that control the operations of the service provider computer 104 may be incorporated into the service provider computer 104 and/or may be in communication with the service provider computer 104 via one or more suitable networks. In certain example embodiments, the operations and/or control of the service provider computer 104 may be distributed among several processing components.

Similar to the eligibility sponsor computer 102, the service provider computer 104 may include one or more processors 130, one or more memory devices 132, one or more input/output ("I/O") interfaces 134, and one or more network interfaces 136. The one or more memory devices 132 may be any suitable memory device, for example, caches, read-only memory devices, random access memory devices, magnetic storage devices, removable storage devices, etc. The one or more memory devices 132 may store data, executable instructions, and/or various program modules utilized by the service provider computer 104, for example, data files 138, an operating system ("OS") 140, a host module 142, a pre- and post-edit (PPE) module 144, and a database management system (DBMS) 146 to facilitate management of data files 138 and other data stored in the memory devices 132 and/or one or more databases 128. The OS 140 may be any operating system known in the art or which may be developed in the future including, but not limited to, Microsoft Windows®, Apple OSX™, Linux, Unix, Apple iOS™, Google Android™, or a mainframe operating system. The OS 140 may be a suitable software module that controls the general operation of the service provider computer 104 and/or that facilitates the execution of other software modules.

The PPE module 144 may be operable to perform one or more pre-edits on a received healthcare transaction, such as predetermination of benefits transactions, healthcare claim transactions, prescription claim transaction or billing requests, healthcare order transactions, or e-prescription transactions (e.g., electronic prescription order transactions, e-scripts, or e-prescriptions), prior to routing or otherwise communicating the received healthcare transaction to a suitable claims processor computer 108 or another destination of the transaction. Additionally, the PPE module 144 may be operable to perform one or more post-edits on an adjudicated response that is received from a claims processor computer 108 for a healthcare transaction prior to routing the adjudicated response to the pharmacy computer 106. A wide variety of different pre-edits and/or post edits may be performed as desired in various embodiments of the disclosure. In certain example embodiments, an eligibility services module 148 and its functions may be incorporated into the PPE 144 and/or may be in communication with the PPE module 144. Alternatively, the functions of the eligibility services module 148 may be, or be part of, another module of the service provider computer 104 or a separate computer from the service provider computer 104. In one example embodiment, the functions of the eligibility services module 148 may be incorporated into the pharmacy computer 106 and operable with the service provider computer 104, such as in the form of an application programming interface.

An eligibility services module 148 or an eligibility services application may also be operative with the service provider computer 104. The eligibility services module 148 may include computer-executable instructions operable for facilitating the communication of one or more intervention services available for an eligible patient. For example, the eligibility services module 148 may facilitate receipt of patient eligibility files including, for example, one or more intervention services available for an eligible patient. The patient eligibility file may include, for example, patient identification information (e.g., a patient's first and/or last name, a patient's social security number, a patient's health insurance claim number (HICN), a patient's gender, a patient's address/zip code, etc.), patient contact information (e.g., patient address, phone number, or email address), and/or eligible intervention services information (e.g., wellness screening services, MTM services, immunization messaging, cash prescription monitoring, refill adherence, high-risk medication monitoring, and diabetic screening or monitoring, etc.). In one example, eligible intervention services information may include, without limitation, an eligibility group, an eligibility type, an eligibility initiation, and/or an eligibility termination. The eligibility services module 148 may facilitate storage of data included in the patient eligibility file in one or more suitable databases and/or data storage devices, such as database 128.

In operation, the eligibility services module 148 may receive information associated with a healthcare transaction, such as a prescription claim transaction and/or an adjudicated response. In addition, the eligibility services module 148 may be further operable to access and/or be in communication with the eligibility sponsor computer 102. In one example, the eligibility services module 148 may access and/or be in communication with the eligibility sponsor computer 102 to identify a patient eligibility file available for the healthcare transaction and/or the adjudicated response. The eligibility services module 148 may utilize the patient eligibility file to determine intervention services that may be available to the particular patient identified in the corresponding healthcare transaction and/or the adjudicated response. In addition, the eligibility services module 148 may be further operable to identify one or more parameters to be collected during the intervention service available to the patient. The eligibility services module 148 may be further operable to generate rejections to healthcare transactions and insert codes and/or messages requesting a parameter to be collected during the intervention service. The eligibility service module 148 may be further operable to receive resubmitted healthcare transactions and determine if the requested parameter for the patient is included in the resubmitted transaction. If the requested parameter is not included, the eligibility services module 148 may be further operable to identify a code and/or message in the resubmitted transaction and determine why the requested parameter was not included in the resubmitted transaction based on that code and/or message. The eligibility services module 148 may also be operable to determine if additional parameters are needed and may continue to generate reject responses and insert codes and/or messages into the reject responses that identify the parameter to obtain from the patient for the particular intervention service. The eligibility services module 148 may further be operable, alone or in conjunction with the service provider computer 104, the parameters obtained during the intervention service to the claims processor computer 108. In addition, the eligibility services module 148 may be further operable to generate and communicate an approval response to the pharmacy computer 106. The approval response, in one example, may indicate that the intervention service has been completed and all the necessary parameters for the intervention service have been received. The eligibility services module 148 may be further operable to facilitate storage of data, including the screening parameters received for the patient as part of the intervention service, in one or more suitable databases and/or data storage devices, such as the database 128.

According to an example embodiment, the data files 138 may store healthcare transaction records associated with communications received from various eligibility sponsor computers 102, and/or various pharmacy computers 106, and/or various claims processor computers 108. The data files 138 may also store any number of suitable routing tables that facilitate determining the destination of communications received from an eligibility sponsor computer 102, a pharmacy computer 106, and/or a claims processor computer 108.

In one or more example embodiments of the disclosure, the service provider computer 104 and/or the eligibility services module 148 (either alone or as part of the service provider computer 104) may include or otherwise be in communication with one or more suitable databases and/or data storage devices 128, which may include, but are not limited to, one or more patient eligibility information files 150, one or more eligible claims processor files 152, one or more intervention parameter files 154, one or more collected patient parameter files 156, and one or more pharmacy eligibility files 158.

The patient eligibility information files 150 may include, without limitation, information captured by eligibility sponsor computers 102 and delivered to the service provider computer 104. For example, the patient eligibility information files 150 may include patient data such as a patient identifier (e.g., patient social security number, a subset of the patient social security number, a health insurance claim number (HICN), cardholder ID, etc.), a patient name, a patient gender, a patient date of birth, an address of the patient, a phone number for the patient, and/or an email address for the patient. The patient eligibility information files 150 may also include eligibility information, for example, without limitation, an eligibility group, an eligibility type, an eligibility initiation, an eligibility termination, and the like for intervention services (such as wellness screening, blood pressure monitoring, MTM services, immunization messaging, cash prescription monitoring, refill adherence, high-risk medication monitoring, and diabetic screening or monitoring, etc.) available to the patient.

The eligible claims processor files 152 may include, without limitation, an identification of the claims processor computers (e.g., by destination identifier (BIN Number, Bin Number and PCN, or BIN Number and Group ID)) for which each type of intervention service is provided (e.g., the claims processor associated with the claims processor computer has contracted to receive intervention notification and parameter retrieval services). The eligible claims processor files 152 may also include destination identifiers one or more claims processor computers 108 for which a healthcare transaction was rejected by the eligibility services module 148 and/or the service provider computer 104 during the processing of a received healthcare transaction, as described herein. The eligible claims processor files 152 may include at least a destination identifier (e.g., BIN Number, BIN Number and PCN, and/or BIN Number and Group ID), a claims processor name, and one or more indicators (e.g., code, name, etc.) identifying the one or more intervention services for which the service provider has agreed to provide notification and/or parameter collection services for the respective claims processor.

The intervention parameter files 154 may include, without limitation, one or more parameters or codes identifying those one or more parameters to obtain from the patient under an intervention service. The intervention parameter files 154 may also include messages that can be inserted into the reject responses and can instruct the recipient of the reject response as to what parameter should be obtained from the patient and included in the next submission of the resubmitted prescription claim transaction. The intervention parameter files 154 may also include the name and/or code (intervention service ID) identifying the intervention service. The parameters, codes identifying the parameters, and/or messages providing instructions regarding collection of the next parameter may be linked or otherwise associated with name or code identifying the corresponding intervention service in the intervention parameter files.

The collected patient parameter files 156 may include, without limitation, one or more patient identifiers, the intervention service ID identifying the intervention service provided to the patient, and one or more patient parameter data representing parameters collected from the patient as part of the intervention service. For example, the patient parameter data may include, but is not limited to, patient blood pressure, patient total cholesterol measurement, patient HDL cholesterol measurement, patient LDL cholesterol measurement, patient triglycerides measurement, patient blood glucose measurement, patient height, patient weight, patient waist measurement, and the like.

The pharmacy eligibility files 158 may include, without limitation, pharmacy information, including, but not limited to, a pharmacy identifier (e.g., National Council for Prescription Drug Programs (NCPDP) Provider ID, National Provider Identifier (NPI), group ID, BIN Number, or the like), a pharmacy and/or pharmacy chain name, a pharmacy email address, a pharmacy fax number, a pharmacy phone number, and/or a pharmacy street address. The pharmacy eligibility files 158 may further include the name and/or code (intervention service ID) of the one or more intervention notifications and parameter collection services being provided to the corresponding pharmacy or pharmacy chain.

The service provider computer 104 may include additional program modules for performing other processing methods described herein. Those of ordinary skill in the art will appreciate that the service provider computer 104 may include alternate and/or additional components, hardware, or software without departing from the scope of the disclosure.

With continued reference to the service provider computer 104, the one or more I/O interfaces 134 may facilitate communication between the service provider computer 104 and one or more input/output devices, for example, one or more user interface devices, such as a display, keypad, control panel, touch screen display, remote control, microphone, etc., that facilitate user interaction with the service provider computer 104. The one or more network interfaces 136 may facilitate connection of the service provider computer 104 to one or more suitable networks, for example, the network 110 illustrated in FIG. 1. In this regard, the service provider computer 104 may communicate with other components of the system 100, such as the eligibility sponsor computer 102, the pharmacy computers 106, the claims processor computers 108 and the database 128.

With continued reference to FIG. 1, any number of pharmacy computers 106 may be associated with (e.g., located within or providing computing services for) any number of pharmacies and/or pharmacists. Each pharmacy computer 106 may be any suitable processor-driven device that facilitates generating, communicating, processing, and/or fulfilling healthcare transactions such as predetermination of benefits transactions, healthcare claim transactions, prescription claim transactions or billing requests, healthcare order transactions, or e-prescription transactions (e.g., electronic prescription order transactions, e-scripts, or e-prescriptions) received from or transmitted to the service provider computer 104. For example, a pharmacy computer 106 may be a processor-driven device associated with (i.e., located within or otherwise providing computing services for) a pharmacy. As desired, the pharmacy computers 106 may include any number of special-purpose computers or other particular machines, application-specific integrated circuits, microcontrollers, personal computers, minicomputers, mainframe computers, servers, and the like. In certain example embodiments, the operations of the pharmacy computers 106 may be controlled by computer-executed or computer-implemented instructions that are executed by one or more processors associated with the pharmacy computer 106 to form a special-purpose computer or other particular machine that is operable to facilitate the receipt, generation, and/or fulfillment of healthcare transactions (e.g., predetermination of benefits transactions, healthcare claim transactions, prescription claim transactions or billing requests, healthcare order transactions, or e-prescription transactions (e.g., electronic prescription order transactions, e-scripts, or e-prescriptions)). The one or more processors that control the operations of the pharmacy computer 106 may be incorporated into the pharmacy computer 106 and/or may be in communication with the pharmacy computer 106 via one or more suitable networks. In certain example embodiments, the operations and/or control of the pharmacy computer 106 may be distributed among several processing components.

Similar to other components of the system 100, each pharmacy computer 106 may include one or more processors 160, one or more memory devices 162, one or more I/O interfaces 164, and one or more network interfaces 166. The one or more memory devices 162 may be any suitable memory devices, for example, caches, read-only memory devices, random access memory devices, magnetic storage devices, removable memory devices, etc. The one or more memory devices 162 may store data, executable instructions, and/or various program modules utilized by the pharmacy computers 106, for example, data files 168, an OS 170, and a pharmacy management module 172. The data files 168 may include any suitable information that is utilized by the pharmacy computers 106. The OS 170 may be a suitable software module that controls the general operation of the pharmacy computer 106. The OS 170 may also facilitate the execution of other software modules by the one or more processors 160. The OS 170 may be any operating system known in the art or which may be developed in the future including, but not limited to, Microsoft Windows®, Apple OSX™ Linux, Unix, Apple iOS™, Google Android™, or a mainframe operating system.

The one or more I/O interfaces 164 may facilitate communication between the pharmacy computer 106 and one or more input/output devices, for example, one or more user interface devices, such as a display, keypad, control panel, touch screen display, remote control, microphone, etc., that facilitate user interaction with the pharmacy computers 106. The one or more network interfaces 166 may facilitate connection of the pharmacy computer 106 to one or more suitable networks, for example, the network 110 illustrated in FIG. 1. In this regard, the pharmacy computer 106 may receive healthcare transactions and/or other communications from the service provider computer 104 and the pharmacy computers 106 may communicate information associated with processing healthcare transactions (e.g., prescription claim transactions) to the service provider computer 104.

The pharmacy management module 172 may be one or more software applications, including a dedicated program, for fulfilling healthcare transaction orders, reading and/or updating medical records (e.g., prescription records), facilitating patient billing, etc., as well as interacting with the service provider computer 104. For example, a pharmacist or other pharmacy employee, may utilize the pharmacy management module 172 in filling a prescription, recording and/or updating a patient's medical prescription history, and billing, generating, preparing, and providing a healthcare transaction to the service provider computer 104. Furthermore, the pharmacy computer 106 may utilize the pharmacy management module 172 to retrieve or otherwise receive data, messages, or responses from the eligibility sponsor computer 102, the service provider computer 104, and/or other components of the system 100.

With continued reference to FIG. 1, each of the claims processor computers 108 may be any suitable processor-driven device that facilitates receiving, processing (e.g., adjudicating), and/or responding to healthcare transactions received from the service provider computer 104. For example, the claims processor computer 108 may be a processor-driven device associated with (e.g., located within or otherwise providing computing services for) a claims processor (e.g., Pharmacy Benefits Manager (PBM), claims payor, healthcare insurance company, Medicare, Medicaid, or other government healthcare insurance payor, Medicare Part D provider, claims clearinghouse, etc.). As desired, the claims processor computer 108 may include any number of special purpose computers or other particular machines, application specific circuits, microcontrollers, personal computers, minicomputers, mainframe computers, servers, and the like. In certain embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or responding to healthcare transactions received from the service provider computer 104. The one or more processors that control the operations of the claims processor computer 108 may be incorporated into the claims processor computer 108 and/or in communication with the claims processor computer 108 via one or more suitable networks. In certain example embodiments of the disclosure, the operation and/or control of the claims processor computer 108 may be distributed amongst several processing components. In an alternate embodiment, the functions of the claims processor computer 108 may be incorporated into the service provider computer 104.

Similar to other components of the system 100, the claims processor computer 108 may include one or more processors 174, one or more memory devices 176, one or more input/output (I/O) interfaces 178, and one or more network interfaces 180. The memory 176 may be any suitable memory devices, for example, caches, read only memory devices, random access memory devices, magnetic storage devices, removable memory devices, etc. The one or more memory devices 176 may store data, executable instructions, and/or various program modules utilized by the claims processor computer 108, for example, data files 182, an operating system (OS) 184, a database management module ("DBMS") 186, and a host module 188. The data files 182 may include any suitable information that is utilized by the claims processor computer 108 to process healthcare transactions, for example, patient profiles, patient insurance information, patient intervention service information, other information associated with a patient, information associated with a healthcare provider, claims processing rules, etc.

The OS 184 may be a suitable software module that controls the general operation of the claims processor computer 108. The OS 184 may also facilitate the execution of other software modules by the one or more processors 174, for example the DBMS 186 and/or the host module 188. The OS 184 may be any operating system known in the art or which may be developed in the future including, but not limited to, Microsoft Windows®, Apple OSX™, Linux, Unix, Apple iOS™, Google Android™, or a mainframe operating system. The DBMS 186 may be a suitable software module that facilitates access and management of one or more databases that are utilized to store information that is utilized by the claims processor computer 108 in various embodiments of the disclosure. The host module 188 may initiate, receive, process, and/or respond to requests, such as healthcare transactions, from the host module 188 of the service provider computer 104. The claims processor computer 108 may include additional program modules for performing other pre-processing or post-processing methods described herein. Those of ordinary skill in the art will appreciate that the claims processor computer 108 may include alternate and/or additional components, hardware or software without departing from example embodiments of the disclosure.

The I/O interface(s) 178 may facilitate communication between the processors 174 and various I/O devices, such as a keyboard, mouse, printer, microphone, speaker, monitor, bar code reader/scanner, RFID reader, and the like. The one or more network interfaces 180 may facilitate connection of the claims processor computer 108 to one or more suitable networks, for example, network 110 illustrated in FIG. 1. In this regard, the claims processor computer 108 may receive healthcare transactions and/or other communications from the service provider computer 104, and the claims processor computer 108 may communicate information associated with the processing and adjudication of the healthcare transactions to the service provider computer 104.

The network 110 may include any telecommunications and/or data network, whether public, private, or a combination thereof, including a local area network, a wide area network, an intranet, the Internet, intermediate handheld data transfer devices, and/or any combination thereof and may be wired and/or wireless, or any combination thereof. The network 110 may also allow for real time, offline, and/or batch transactions to be transmitted between or among the eligibility sponsor computer 102, the service provider computer 104 (including the eligibility services module 148), the pharmacy computer 106, the claims processor computer 108, and the database 128. Various methodologies as described herein, may be practiced in the context of distributed computing environments. Although the service provider computer 104 is shown for simplicity as being in communication with the eligibility sponsor computer 102, the pharmacy computer 106, the claims processor computer 108, or the database 128 via one intervening network 110, it is to be understood that any other network configurations are possible. For example, intervening network 110 may include a plurality of networks, each with devices such as gateways and routers for providing connectivity between or among the components of the system 100. Instead of or in addition to the network 110, dedicated communication links may be used to connect various devices in accordance with an example embodiment. For example, the service provider computer 104 may form the basis of network 110 that interconnects the eligibility sponsor computer 102, the service provider computer 104 (including the eligibility services module 148), the pharmacy computer 106, the claims processor computer 108, and the database 128.

Those of ordinary skill in the art will appreciate that the system 100 shown in and described with respect to FIG. 1 is provided by way of example only. Numerous other operating environments, system architectures, and device and network configurations are possible. Other system embodiments can include fewer or greater numbers of components and may incorporate some or all of the functionality described with respect to the system components shown in FIG. 1. For example, in an exemplary embodiment, the service provider computer 104 (or other computer) may be implemented as a specialized processing machine that includes hardware and/or software for performing the methods described herein. Accordingly, embodiments of the disclosure should not be construed as being limited to any particular operating environment, system architecture, or device or network configuration.

Operational Overview

Certain portions of the exemplary methods below will be described with reference to determining and communicating intervention services (e.g., wellness screening, blood pressure monitoring, MTM services, immunization messaging, cash prescription monitoring, refill adherence, high-risk medication monitoring, and diabetic screening or monitoring, etc.) available to a patient, and determining, communicating, and receiving parameters to collect and patient parameter data collected from the patient for the corresponding intervention service as part of the processing of a healthcare transaction. While the methods described below are described with reference to a prescription claim transaction or billing request, each form of a healthcare transaction, such as a predetermination of benefits transaction, healthcare claim transaction, prescription claim transaction or billing request, healthcare order transaction, or e-prescription transaction (e.g., electronic prescription order transaction, e-script, or e-prescription), should be individually read as being used in the methods described below. In addition, while certain methods below are described with reference to the intervention service being a wellness screening service, this is also for example only and all other intervention services, including but not limited to MTM services, immunization messaging, cash prescription monitoring, refill adherence, high-risk medication monitoring, and diabetic screening or monitoring, should be individually read as being used in the methods below.

Figure 2:
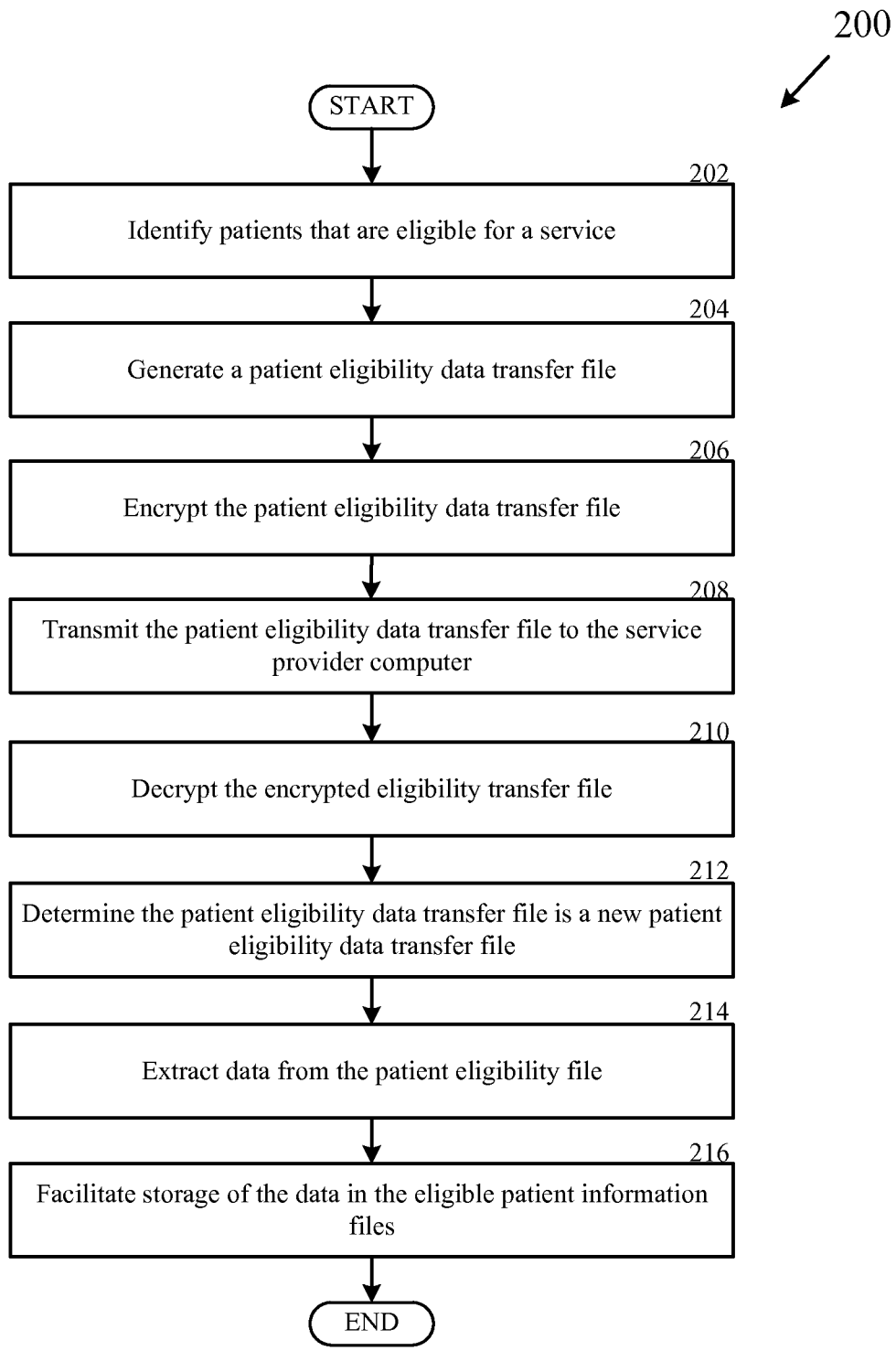
FIG. 2 illustrates a flow chart of an example method for accessing and/or communicating intervention services available for an eligible patient associated with a medication and/or product as part of the processing of a healthcare transaction, according to an example embodiment.

FIG. 2 is a flow chart illustrating an example method 200 for accessing and/or communicating intervention services available for an eligible patient associated with a medication and/or product as part of the processing of a healthcare transaction, according to an example embodiment of the disclosure. Referring now to FIGS. 1 and 2, the exemplary method 200 begins at the START step and continues to step 202, where an eligibility sponsor computer, such as eligibility sponsor computer 102, may identify one or more patients that may be eligible to receive one or more intervention services (e.g., wellness screening, blood pressure monitoring, MTM services, immunization messaging, cash prescription monitoring, refill adherence, high-risk medication monitoring, and diabetic screening or monitoring, etc.). In one example implementation, an eligibility sponsor computer 102 may be associated with a healthcare entity (e.g., a healthcare services corporation) that has contracted with a pharmacy and/or a pharmacy corporation to provide a variety of intervention services including, but not limited to, wellness screening services, MTM services, immunization messaging, cash prescription monitoring, refill adherence, high-risk medication monitoring, and diabetic screening or monitoring, etc.). An MTM service available to a patient may include a broad range of services. For example, without limitation, an MTM may involve a patient assessment, a comprehensive medication review, formulating a medication treatment plan for a patient, enhancing medication adherence through patient education, monitoring efficacy and safety of medication therapy, and the like.

In one example implementation, a patient may be identified as an eligible patient based upon a medication and/or product associated with an intervention service type. In one example implementation, the eligibility sponsor computer 102 may have access to a pharmacy's computer, such as pharmacy computer 106, and records associated with healthcare transactions (e.g., a predetermination of benefits transaction, healthcare claim transaction, prescription claim transaction or billing request, healthcare order transaction, or e-prescription transaction (e.g., electronic prescription order transaction, e-script, or e-prescription). The eligibility sponsor computer 102 may identify from one or more accessed patient records, a patient that may be eligible to receive one or more intervention services. In one example implementation, the identification may be based upon a medication and/or product type (e.g., a medication/product identifier (e.g., NDC code, RxNorm medication identifier, a medication/product name, or the like) identified in an accessed patient record. Alternatively, the identification may be based upon a patient demographic such as, without limitation, a patient age and/or a patient gender.

At step 204, the eligibility sponsor computer 102 may create a patient eligibility transfer file for data associated with the identified patient. For example, based upon a predetermined file format, the eligibility sponsor computer 102 may create the patient eligibility transfer file. In one example implementation, the format for the patient eligibility transfer file may include one or more of the following information:

Header:
Segment ID: "HDR"
Post Date: 9(8)
File type: "Initial load"
Transaction:
Unique Patient ID
BIN Number:
Processor Control Number:
Group ID
Cardholder ID
Person Code
Patient Last Name
Patient First Name
Date of Birth
Social Security #(SSNID)
Patient Gender Code
Patient Street Address 1
Patient Street Address 2
Patient City Address
Patient State/Province Address
Patient ZIP/Postal Zone
Primary Phone Number
Primary Phone Number Type
Alternate Patient Street 1
Alternate Patient Street 2
Alternate Patient City
Alternate Patient State
Alternate Patient ZIP
Alternate Patient Phone #
Alternate Patient Phone # Type
Eligibility Group:
Eligibility Type:
Eligibility Initiation:
Eligibility Termination:
Trailer:
Segment Identifier: "TRL"
Count: "NNNNNNN"

At step 206, the eligibility sponsor computer 102 may encrypt the created patient eligibility transfer file. In one example implementation, the encryption utilized by the eligibility sponsor computer 102 may be an encryption method predetermined by the eligibility sponsor computer 102, the service provider computer 104, and/or the pharmacy computer 106. For example, the encryption method may include, without limitation, hashing, private-key cryptography, public-key cryptography, or the like.

At step 208, the eligibility sponsor computer 102 may communicate an encrypted patient eligibility transfer file to the eligibility services module 148 or another portion of the service provider computer 104. At step 210, the eligibility services module 148 may decrypt the encrypted patient eligibility transfer file. In one example implementation, the eligibility services module 148 may receive, in, for example, a separate communication, means for decrypting the encrypted patient eligibility transfer file. For example, in a prior, subsequent, or concurrent communication, the eligibility services module 148 may receive a key necessary to decrypt the encrypted patient eligibility transfer file.

At step 212, the eligibility services module 148 may determine that the decrypted patient eligibility file is a file that contains new patient data. In one example implementation, the eligibility services module 148 may determine that the decrypted patient eligibility transfer file contains new data by parsing the header of the file. For example, the eligibility services module 148 may parse the header of the file and determine that the file type is an "initial load", meaning, the decrypted patient eligibility transfer file contains new patient data. In another non-limiting example, the patient eligibility data transfer file may be named in such a way as to indicate it is an initial setup file (e.g., File Name: "Initial Setup Patient Eligibility Data Transfer File").

At step 214, the eligibility services module 148 may extract the data from the patient eligibility transfer file. At step 216, the eligibility services module 148 may facilitate storage of the patient data included in the patient eligibility transfer file. In one example implementation, the extracted data may be stored in a file included in the one or more patient eligibility information files 150. The process may then proceed to the END step.

Figure 3:
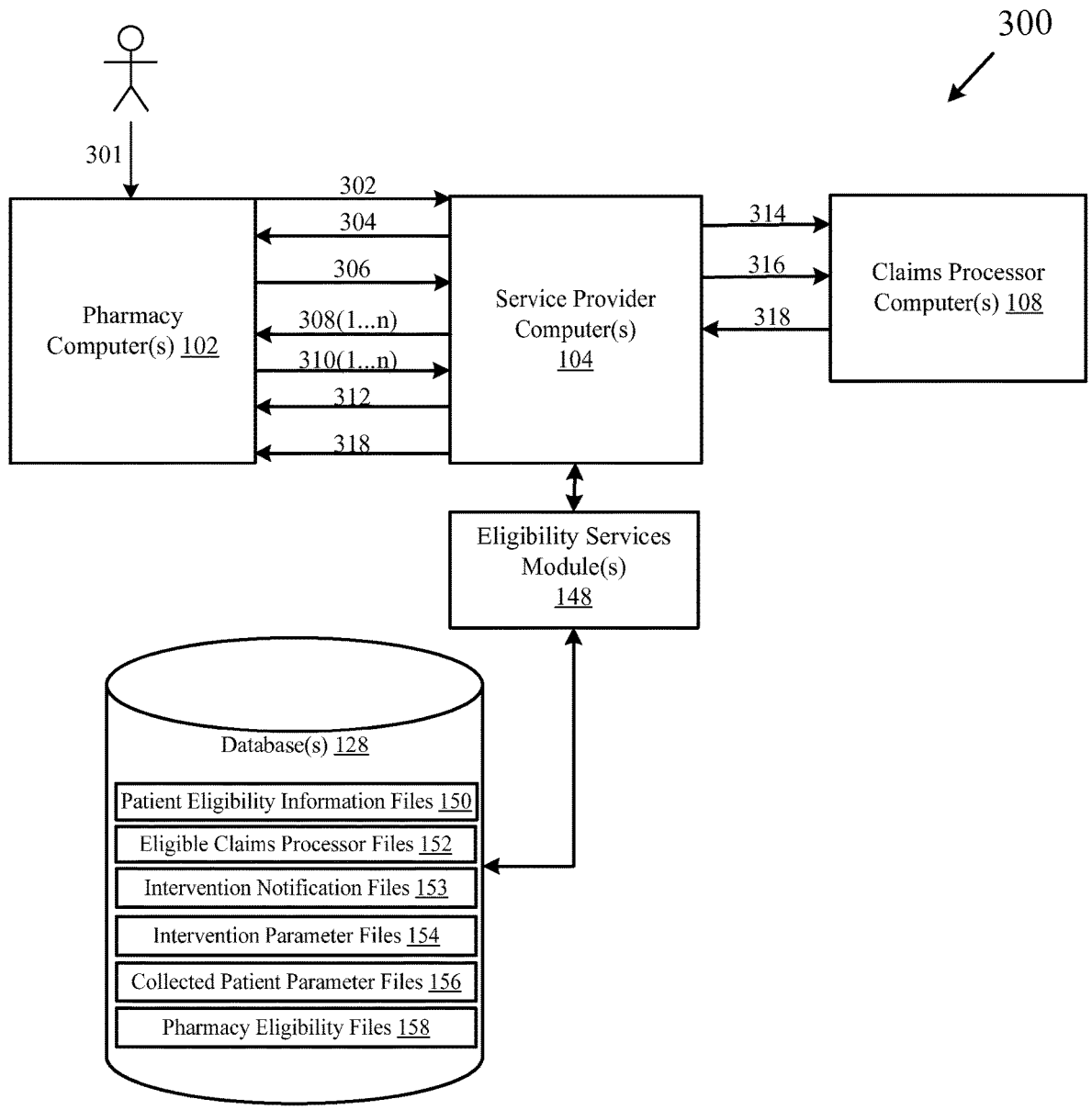
FIG. 3 illustrates an example block diagram for a method for determining, collecting, configuring, and transmitting information derived during an intervention services, such as a wellness screening, available for an eligible patient, according to an example embodiment.
Figure 4B:
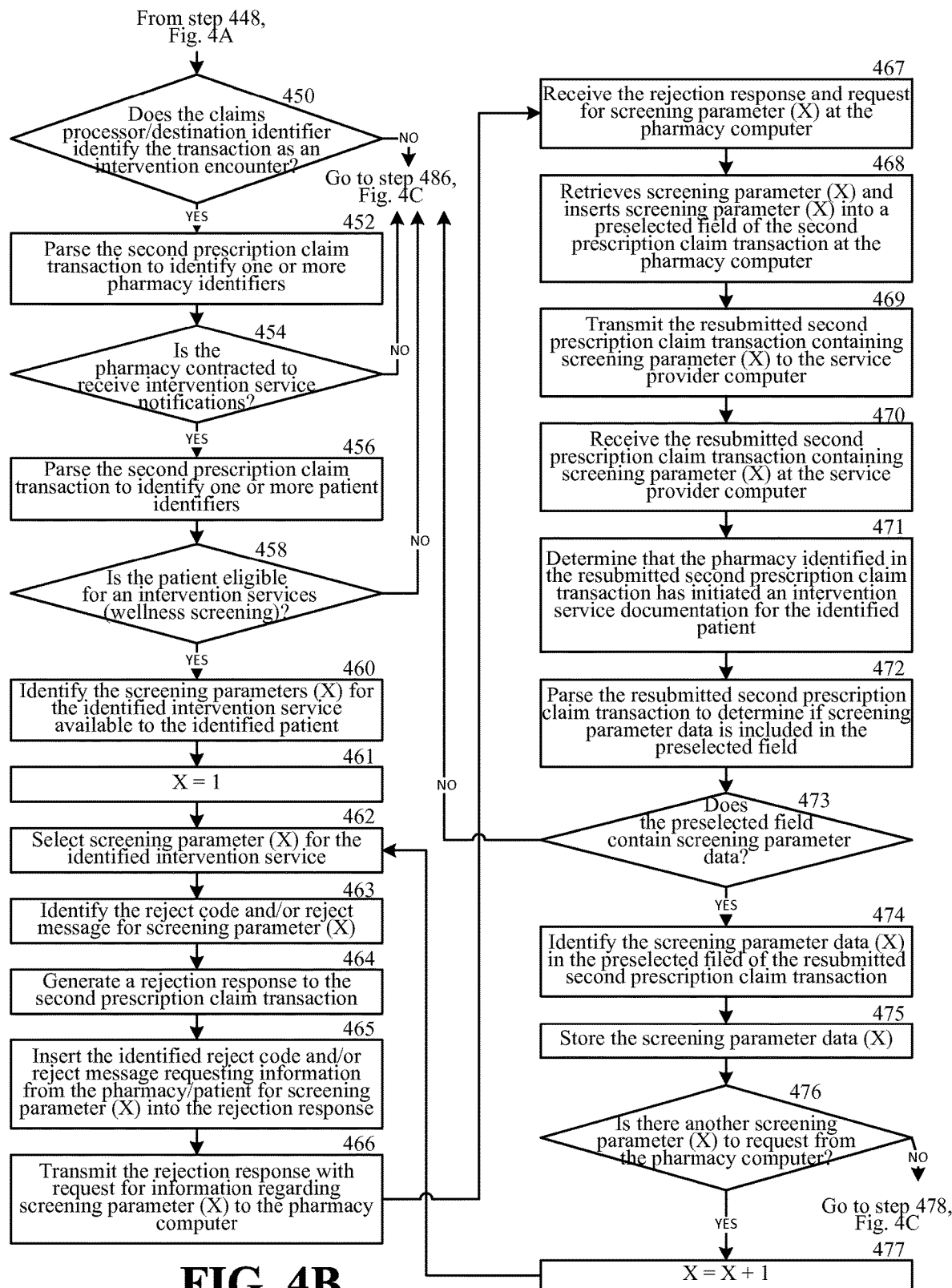
Figure 4C:
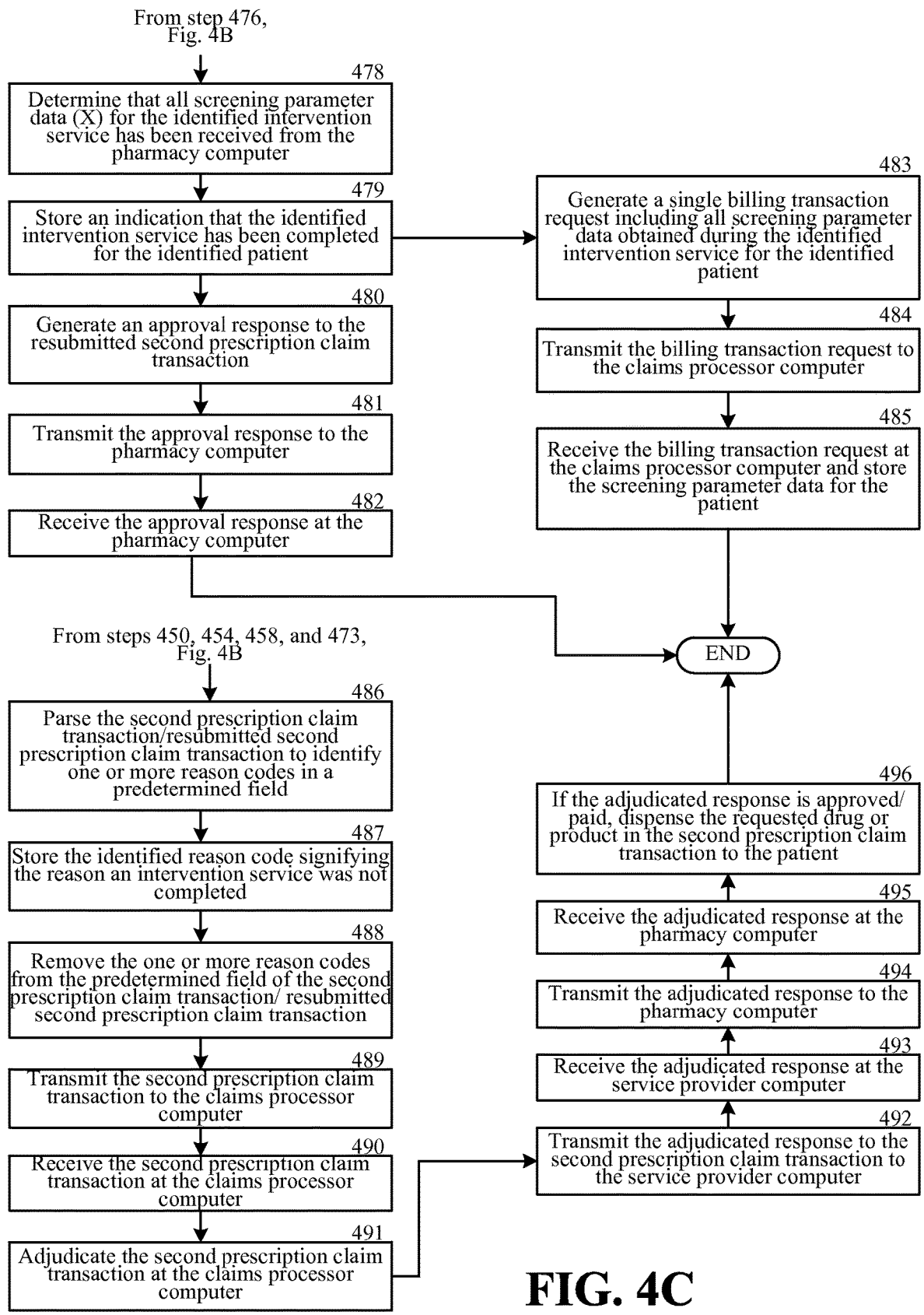

FIG. 3 illustrates an example block diagram for a method for determining, collecting, configuring, and transmitting information derived during an intervention services, such as a wellness screening, available for an eligible patient, according to an example embodiment of the disclosure. FIGS. 4A-C are a flowchart illustrating an example method 400 for determining, collecting, configuring, and transmitting information derived during an intervention service, such as a wellness screening, available for an eligible patient, according to an example embodiment of the disclosure. The block diagram 300 of FIG. 3 will be discussed in conjunction with the method 400 of FIGS. 4A-C.

Referring now to FIGS. 1, 3, and 4A-C the exemplary method 400 begins at the START step and proceeds to step 402, where a prescription/order request 301 is received. In one example embodiment, the prescription/order request 301 is received by a pharmacist at a pharmacy. The prescription/order request 301 may be received from a patient, another healthcare provider prescribing a medication or service (e.g., physician, clinic, physician's office, hospital, etc.), by phone, via the Internet, via an e-prescription transaction or by way of an electronic system order. For example, the prescription 301 may be received by the patient from a prescriber of the medication, such as a doctor, dentist, nurse, physician's assistant, or any other person authorized to prescribe medications, products, and/or services for a patient. The patient may go to the location of the pharmacy and physically hand the prescription request 301 to the pharmacist or make a request via a web portal communicably coupled to the pharmacy computer 106 or an IVR communicably coupled or otherwise providing order data to the pharmacy computer 106. The pharmacist determines the patient's name and accesses the pharmacy computer 106, which receives a selection of patient information from the pharmacist via the I/O interface 164 in step 404. For example, the pharmacist accesses the pharmacy computer 106 and accesses a database of patient information, which may be stored in memory 162 or in another database either local or remote from the pharmacy computer 106. The pharmacist can then select the name or other patient identification information in the patient information database that matches the name or other identification information of the patient.

In step 406, a prescription claim transaction 302 is generated and/or formatted at the pharmacy computer 106. In certain exemplary embodiments, the pharmacy computer 106 formats the prescription claim transaction 302 with patient information (e.g., patient identifiers), Payor ID/routing information (e.g., claims processor/destination identifiers), and medication information (e.g., medication identifiers). The information can be input into the healthcare claim transaction 302 by the pharmacist via the I/O interface 164 or automatically retrieved and entered by the pharmacy computer 106 and, in certain situations, can be based at least in part on historical transaction information for the patient in the data files 168 or a database communicably coupled to the pharmacy computer 106. According to one example embodiment, the prescription claim transaction 302 may be formatted in accordance with a version of the National Council for Prescription Drug Programs (NCPDP) Telecommunication Standard, although other standards, such as ANSI ASC X-12 Standard, Health Level 7 (HL7) Standard, or NCPDP Script Standard may be utilized as well.

As discussed above, the prescription claim transaction 302 may include a BIN Number, a BIN Number and PCN, or a BIN Number and Group ID for identifying a particular claims processor computer (e.g., ACO, PBM, payor, healthcare insurance company, Medicare or other government healthcare insurance payor, Medicare Part D provider, etc.), such as the claims processor computer 108, as a destination for the prescription claim transaction 302. In addition, the prescription claim transaction 302 may also include information relating to the patient, payor, prescriber, healthcare provider, and/or the requested medication. As an example, the prescription claim transaction 302 may include one or more of the following information:

Payor ID/Routing Information (Destination Identifier)
BIN Number, BIN Number and PCN and/or BIN Number and Group ID, that designates a destination of the prescription claim transaction 302
Patient Information
Name (e.g. Patient Last Name, Patient First Name, etc.)
Date of Birth of Patient
Age of Patient
Gender of Patient
Patient Address (e.g. Street Address, City, State, Zip/Postal Code, etc.)
Patient Contact Information (e.g. Patient Telephone Number, Email Address, etc.)
Patient Health Condition Information
Patient ID or other identifier (e.g., Health Insurance Claim Number (HICN), Social Security Number, etc.)
Insurance/Coverage Information
Cardholder Name (e.g. Cardholder First Name, Cardholder Last Name)
Cardholder ID and/or other identifier (e.g. Person Code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number, Email Address, Fax Number, etc.)
Pharmacy or other Healthcare Provider Information (e.g. Store Name, Chain Identifier, etc.)
Pharmacy or other Healthcare Provider ID (e.g. NPI code)
Claim Information
Drug, service, or product information (e.g. National Drug Code (NDC) code, RxNorm code, etc.)
Prescription/Service Reference Number
Date Prescription Written
Quantity Dispensed
Days' Supply
Diagnosis/Condition (e.g., Diagnosis Code (e.g., International Statistical Classification of Diseases and Related Health Problems (ICD) Diagnosis Code)
Pricing information for the drug/service/product (e.g. Network Price, Usual & Customary price)
Number of Refills Authorized
One or more NCPDP Message Fields
One or more Drug Utilization (DUR) Codes
Date of Service.

The prescription claim transaction 302 can be used to determine if the claims processor associated with the claims processor computer 108 approves or rejects payment coverage for medication being requested in the prescription claim transaction 302 and, if approved, the amount the claims processor will cover (or pay) for the medication being requested and how much the patient co-pay amount will be.

The pharmacy computer 106 can transmit the first prescription claim transaction 302 to the service provider computer 104 in step 408. In step 410, the service provider computer 104 receives the first prescription claim transaction 302. For example, the first prescription claim transaction 302 can be transmitted by the pharmacy computer 106 to the service provider computer 104 via the network 110. The service provider computer 104 may conduct any pre-editing, if necessary, on the first prescription claim transaction 302 in step 412. The pre-edits may include verifying, adding, and/or editing information included in the first prescription claim transaction 302 prior to it being communicated to a claims processor computer 108. For example, the service provider computer 104 can parse the first prescription claim transaction 302 to determine/edit the financial fields, the service code, the quantity dispensed, and or the patient age.

In step 414, the eligibility services module 148 or another portion of the service provider computer 104 may identify a pharmacy identifier in the first prescription claim transaction 302. In one example, the eligibility services module 148 or another portion of the service provider computer 104 may parse the received first prescription claim transaction 302 to identify a pharmacy identifier (e.g., a pharmacy name, NPI number, chain identifier, etc.) in one or more fields of the first prescription claim transaction 302.

In step 416, an inquiry is conducted to determine if the pharmacy corresponding to the parsed pharmacy identifier is contracted to receive intervention service notifications. In one example embodiment, intervention service notification includes the eligibility services module 148 or another portion of the service provider computer 104 notifying the pharmacy computer 106, via a transaction response, that the patient is eligible to receive an intervention service. In one example, a contracted pharmacy may be a pharmacy or group of pharmacies (e.g., pharmacy chain) that has contracted with the service provider associated with the service provider computer 104 to receive intervention service notifications, and thereby enable or activate the eligibility services module 148 for use in processing healthcare transactions, like the prescription claim transaction 302, that are routed or otherwise communicated to the service provider computer 104. For example, the service provider computer 104 may compare the identified pharmacy identifier (e.g., a pharmacy name, NPI code, pharmacy chain identifier, etc.) to a table, schedule, or list of pharmacy identifiers for those pharmacies that have contracted to receive intervention service notifications to determine if a match exists. If a match exists, the pharmacy identified by the pharmacy identifier in the prescription claim transaction 302 (e.g., the pharmacy associated with the pharmacy computer 106) is determined to be contracted, and the YES branch is followed to step 418. If a match is not identified, the pharmacy identified by the pharmacy identifier in the first prescription claim transaction 302 (e.g., the pharmacy associated with the pharmacy computer 106) is not contracted, and the NO branch is followed and processing may proceed to step 426.

In step 418, processing of the prescription claim transaction 302 may further include an identification of a corresponding claims processor computer 108 represented by the destination identifier in the prescription claim transaction 302. In one example embodiment, the eligibility services module 148 or another portion of the service provider computer 104 may parse the prescription claim transaction 302 to identify at least a destination identifier (e.g., BIN Number, BIN Number and PCN, or BIN Number and Group ID). At step 420, an inquiry is conducted to determine if the claims processor associated with claims processor computer and identified by the destination identifier is contracted to receive intervention services. In one example embodiment, the determination is made by the eligibility services module 148 or another portion of the service provider computer 104. In one example, the eligibility services module 148 or another portion of the service provider computer 104 may compare the identified destination identifier to one or more schedules, lists, or tables within the eligible claims processor files 152 to determine if one or more of the records in the eligibility claims processor files includes a destination identifier that matches the destination identifier in the prescription claim transaction 302. If the destination identifier does exist in at least one of the records in the eligible claims processor files 152, then a match exists, and the YES branch is followed to step 422. On the other hand, if a match to the destination identifier does not exist in any of the records in the eligible claims processor files 152, then a match does not exist and the NO branch is followed to step 426.

In step 422, processing of the prescription claim transaction 302 may further include an identification of one or more patient identifiers in the prescription claim transaction 302. In one example, the eligibility services module 148 or another portion of the service provider computer 104 may parse the prescription claim transaction 302 to identify one or more patient identifiers (e.g., a patient social security number, a subset of the patient social security number, health insurance claim number (HICN), cardholder ID, a patient first name, patient last name, patient date of birth, patient gender, patient address, patient zip/postal code, etc.). In step 424, an inquiry is conducted to determine if the patient identified by the patient identifiers is eligible for an intervention service (e.g., wellness screening, blood pressure monitoring, MTM services, immunization messaging, cash prescription monitoring, refill adherence, high-risk medication monitoring, and diabetic screening or monitoring, etc.). In one example, the determination may be made by the eligibility services module 148 or another portion of the service provider computer 104. In one example implementation, the service provider computer 104 may employ the eligibility services module 148 to access the patient eligibility information files 150. The patient eligibility information files 150 may include information provided by the eligibility sponsor computer 102. For example, the patient eligibility information files 150 may include at least a patient identifier, patient demographics (e.g., patient gender, patient age, patient date of birth, patient street address, patient zip/postal code etc.), an eligibility group, and/or an eligibility type. The eligibility services module 148 or another portion of the service provider computer 104 may compare the identified one or more patient identifiers from the prescription claim transaction 302 to the patient information in the patient eligibility information files 150. For example, the eligibility services module 148 or anther portion of the service provider computer 104 may parse the patient eligibility information files 150 to determine if the identified one or more patient identifiers matches a patient identifier in the files 150. Matching may include determinative matching and/or probabilistic matching. Under probabilistic matching, all or a portion of the received patient identifier data may be compared to data in the patient eligibility information files 150. Using probabilistic matching, the module 148 can generate a percentage or score for each stored record that can represent the likelihood that each stored record matches the patient for which the prescription claim transaction 302 is being submitted. Each percentage or score for each record can be compared to a predetermined threshold score to determine if the record should be identified as a matching record. The predetermined threshold score is adjustable and can be determined based on the level of certainty desired. If a match is not identified, the patient is ineligible at this time for an intervention service and the NO branch is followed to step 426. In step 426, the service provider computer 104 may transmit the prescription claim transaction 302 to the claims processor computer 108 associated with the destination identifier in the transaction 302. The process may then continue to step 491 of FIG. 4C. Returning to the inquiry of step 424, if a match exists, the patient is eligible for an intervention service and the YES branch is followed to step 428.

In step 428, processing of the prescription claim transaction 302 may further include an inquiry to determine if notification of the intervention service available for the eligible patient has previously been transmitted or otherwise communicated to the pharmacy. In one example embodiment, the determination may be made by the eligibility services module 148 or another portion of the service provider computer 104. The determination may be based at least in part on whether the patient (separate from the pharmacy) has previously received notification of the available intervention service. Alternatively and/or additionally, the determination may be based at least in part upon whether an override code has been submitted along with and/or is contained within the prescription claim transaction 302, and/or the prescription claim transaction 302 coincides with an interval between notification periods for the available service. In one example embodiment, the service provider computer 104 may employ the eligibility services module 148 to access the intervention notification files 153 from the database 128. The eligibility services module 148 or another portion of the service provider computer 104 may compare the identified patient identifier to the patient information in the intervention notification files 153. For example, the eligibility services module 148 may parse the intervention notification files 153 to determine if the identified patient identifier matches a patient identifier in the intervention notification files 153. If a match is identified, the eligibility services module 148 or another portion of the service provider computer 104 may further determine whether the identified patient identifier found in the intervention notification files 153 includes a file for the corresponding available services. The determination may, for example, be based upon a medication and/or product identifier included in the identified file for the identified patient. Alternatively and/or additionally, the determination may be based upon a corresponding service code or type included in the identified file associated with the available intervention service. If notification of the available service has previously been communicated to the pharmacy (or patient), then the YES branch is followed to step 450 of FIG. 4B. If a match does not exist and notification of the available service has not previously been communicated to the pharmacy (or patient), then the NO branch is followed to step 430.

In step 430, the eligibility services module 148 or another portion of the service provider computer 104 can generate a reject response 304 to the prescription claim transaction 302. In one example implementation, the service provider computer 104 may employ the eligibility services module 148 to insert or otherwise append an available intervention services notification to the reject response 304. The available intervention services notification and reject response 304 may include at least a reject code indicating the reason why the prescription claim transaction 302 was rejected and/or a rejection message provided in text field of the reject response 304 communicating to the pharmacist associated with the pharmacy computer 106 that intervention services are available for the patient. For example, the reject response 304 may include:

Reject Code: "XX"

Message: "Intervention opportunity—patient is eligible for an intervention service. Outreach to patient. As a reminder, bill-document intervention service parameters to Plan ID: XXXXXXX [destination identifier that identifies the transaction as being for an intervention encounter]. Resubmit this claim"

More specifically, when the intervention service is a wellness screening for the patient, such as in one example embodiment, the reject response 304 may include:

Reject Code: "XX"

Message: "Patient eligible for annual (no charge) Wellness Screening. Outreach to patient. As a reminder, bill-document Wellness Screening results to Plan ID: XXXXXXX. Resubmit this claim"

In step 432, the eligibility services module 148 or another portion of the service provider computer 104 may capture that a notification for available intervention service was communicated to the pharmacy computer 106. In one example implementation, the information associated with the notification may be captured and stored in the identified file in the intervention notification files 153. Alternatively and/or additionally, the information associated with the notification may be captured and stored in a patient eligibility information file 150 corresponding to the identified patient.

In step 434, the service provider computer 104 may transmit the reject response 304 to the pharmacy computer 106 via, for example, the network 110. In step 436, the pharmacy computer 106 can receive the reject response 304 and the pharmacist or other employee of the pharmacy associated with the pharmacy computer 106 may review the reject response 304. During the review of the reject response 304, the pharmacist, for example, may identify the reject code and/or the reject message included in the reject response 304 and notification that the patient is eligible to receive an intervention service. After reviewing the rejection message included in the reject response 304, in step 438, pharmacist or other pharmacy employee may generate, via the pharmacy computer 106 a second prescription claim transaction 306. In one example embodiment, the second prescription claim transaction 306 may include the one or more of the same patient identifiers as those included in the first prescription claim transaction 302. The second prescription claim transaction 306 may be a new transaction or a resubmission of the first prescription claim transaction 302. For example, for a variety of potential reasons, pharmacist or other pharmacy employee may not provide the intervention service to the patient and may instead simply resubmit the first prescription claim transaction requesting a medication or product for the patient. In this example, the resubmitted first prescription claim transaction may include the same prescription number, date of service, BIN Number, and/or pharmacy identifier as that which was in the first prescription claim transaction 302. In certain example embodiments where the intervention service is not provided to the patient, the resubmitted first prescription claim transaction 302 may also include an override code and another code or message indicating why the intervention service was not provided to the patient. The pharmacy computer 106 can transmit, via, for example, the network 110, the prescription claim transaction 306 to the service provider computer 104 in step 440.

In step 442, the service provider computer 104 can receive the prescription claim transaction 306 via the host module 172 or another portion of the service provider computer 104. In step 444, the PPE module 144 or another portion of the service provider computer 104 can parse the prescription claim transaction 306 to identify a transaction type identifier. In step 446, an inquiry can be conducted to determine if the parsed transaction type identifier identifies the prescription claim transaction 306 as a billing transaction. In one example embodiment, the PPE module can compare the parsed transaction type identifier to a schedule, listing, or table of transaction type information in, for example, the database 128 or memory 132 to determine if the parsed identifier matches identifiers of a billing transaction. If the transaction type identifier does not identify the transaction 306 as a billing transaction, the process can be followed to the END step and the transaction 306 can be processed in another manner. On the other hand, if the transaction type identifier does identify the transaction 306 as a billing transaction, the YES branch can be followed to step 448.

In step 448, processing of the prescription claim transaction 306 may further include an identification of a destination identifier in the prescription claim transaction 306. In one example embodiment, the eligibility services module 148 or another portion of the service provider computer 104 may parse the prescription claim transaction 306 to identify at least a destination identifier (e.g., BIN Number, BIN Number and PCN, or BIN Number and Group ID). In step 450, an inquiry is conducted to determine if the destination identifier identifies the transaction as an intervention encounter (such as by including the plan ID described above in the reject response 304). In one example embodiment, the determination is made by the eligibility services module 148 or another portion of the service provider computer 104. In one example, the eligibility services module 148 or another portion of the service provider computer 104 may compare the identified destination identifier to one or more schedules, lists, or tables of records of destination identifiers representing intervention encounters in, for example, the database 128 or memory 132 to determine if the destination identifier in the prescription claim transaction 306 matches one or more of the records. If the destination identifier does exist in at least one of the records, then a match exists, and the YES branch is followed to step 452. On the other hand, if a match to the destination identifier does not exist in any of the records, then a match does not exist and the NO branch is followed to step 486 of FIG. 4C.

In an another example embodiment, instead of or prior to steps 448 and 450 above, the eligibility service module 148 or another portion of the service provider computer may parse the second prescription claim transaction 306 to identify and evaluate data in certain fields to determine if the second prescription claim transaction 306 is a resubmission of the first prescription claim transaction 302. For example, the eligibility services module can identify one or more of the prescription number, date of service, fill number (the number of the current refill for the particular transaction), and/or pharmacy identifier in the second prescription claim transaction 306 and compare that to the corresponding one or more of the prescription number, date of service, fill number, and/or pharmacy identifier in the first prescription claim transaction 302 to determine if the data elements compared from the second prescription claim transaction 306 match the corresponding data elements in the first prescription claim transaction 302. Data from the first prescription claim transaction may be retrieved from the database 128 or memory 132. For example, data from the first prescription claim transaction 302 may be stored along with an indication that a message indicating an intervention service for the patient was sent to the pharmacy computer 106. If, for example, the eligibility services module 148 determines that all or a predetermined number or percentage of the selected data match, the eligibility service module 148 may determine that the second prescription claim transaction 306 is a resubmission of the first prescription claim transaction 302. The eligibility services module 148 may further determine, based on information in the database 128 or memory 132 associated with the first prescription claim transaction 302 that a message has been previously sent to the pharmacy computer 106 indicating an intervention service was available for the patient. Based on the positive determination that the second prescription claim transaction 306 is a resubmitted first prescription claim transaction 302 and a message was previously sent to the pharmacy computer 106 (or optionally a computer at another pharmacy at the same or prior point in time) indicating that an intervention service was available for the patient identified in the transaction 306, the process may then proceed to step 486 of FIG. 4C. Alternatively, in addition, the eligibility services module may parse the second prescription claim transaction 306 to determine if the transaction 306 includes a reason code. Based on a positive determination that the second prescription claim transaction includes a reason code, the process may then proceed to step 486 of FIG. 4C.

In step 452, the eligibility services module 148 or another portion of the service provider computer 104 may identify a pharmacy identifier in the prescription claim transaction 306. In one example, the eligibility services module 148 or another portion of the service provider computer 104 may parse the received prescription claim transaction 306 to identify a pharmacy identifier (e.g., a pharmacy name, NPI number, chain identifier, etc.) in one or more fields of the prescription claim transaction 306. In step 454, an inquiry is conducted to determine if the pharmacy corresponding to the parsed pharmacy identifier is contracted to receive intervention service notifications. In one example, the determination is made in a manner substantially similar to that described in step 416. For example, the eligibility services module 148 or another portion of the service provider computer 104 may compare the identified pharmacy identifier (e.g., a pharmacy name, NPI code, pharmacy chain identifier, etc.) to a table, schedule, or list of pharmacy identifiers, for example in the pharmacy eligibility files 158, for those pharmacies that have contracted to receive intervention service notifications to determine if a match exists. If a match exists, the pharmacy identified by the pharmacy identifier in the prescription claim transaction 306 (e.g., the pharmacy associated with the pharmacy computer 106) is determined to be contracted, and the YES branch is followed to step 456. If a match is not identified, the pharmacy identified by the pharmacy identifier in the prescription claim transaction 306 is not contracted, and the NO branch is followed to step 486 of FIG. 4C.

In step 456, processing of the prescription claim transaction 306 may further include an identification of one or more patient identifiers in the prescription claim transaction 306. In one example, the eligibility services module 148 or another portion of the service provider computer 104 may parse the prescription claim transaction 306 to identify one or more patient identifiers (e.g., a patient social security number, a subset of the patient social security number, health insurance claim number (HICN), cardholder ID, a patient first name, patient last name, patient date of birth, patient gender, patient address, patient zip/postal code, etc.). In step 458, an inquiry is conducted to determine if the patient identified by the patient identifiers is eligible for the particular intervention service (e.g., wellness screening, blood pressure monitoring, MTM services, immunization messaging, cash prescription monitoring, refill adherence, high-risk medication monitoring, and diabetic screening or monitoring, etc.) identified with regard to the destination identifier in step 450. In one example, the determination may be made by the eligibility services module 148 or another portion of the service provider computer 104. In one example implementation, the service provider computer 104 may employ the eligibility services module 148 to access the patient eligibility information files 150. The patient eligibility information files 150 may include information provided by the eligibility sponsor computer 102. For example, the patient eligibility information files 150 may include at least a patient identifier, patient demographics (e.g., patient gender, patient age, patient date of birth, patient street address, patient zip/postal code etc.), an eligibility group, and/or an eligibility type. The eligibility services module 148 or another portion of the service provider computer 104 may compare the identified one or more patient identifiers from the prescription claim transaction 306 to the patient information in the patient eligibility information files 150. For example, the eligibility services module 148 or another portion of the service provider computer 104 may parse the patient eligibility information files 150 to determine if the identified one or more patient identifiers matches a patient identifier in the files 150. Matching may include determinative matching and/or probabilistic matching as described hereinabove. For any matching record, a further evaluation may be made to determine if the intervention service identified by the destination identifier is an intervention service that is available for the identified patient. If a match is not identified, the patient is ineligible at this time for an intervention service and the NO branch is followed to step 486 of FIG. 4C. On the other hand, if a patient match is identified and the matching patient record further matches the intervention service represented by the destination identifier in the prescription claim transaction 306, then the YES branch is followed to step 460.

In step 460, the eligibility services module 148 or another portion of the service provider computer, may identify screening parameters (X) to be obtained from the patient for the intervention service identified in the prescription claim transaction 306 by the destination identifier. In one example embodiment, one or more screening parameters may need to be obtained from the patient and communicated back to the service provider computer 104 via the pharmacy computer 106. The number of screening parameters (X) may be determined based on the intervention service and the claims processor associated with the destination identifier and paying the pharmacy associated with the pharmacy computer 104 for conducting the intervention service. In one example embodiment, the screening parameters (X), as well as associated reject codes and rejection messages may be obtained from the intervention parameter files 154 based on the identified type of intervention encounter.

Steps 461-477 below will be described with regard to the intervention service being a wellness screening for the patient. However, this is for example purposes only and other intervention services including, but not limited to, MTM services, immunization messaging, cash prescription monitoring, refill adherence, high-risk medication monitoring, and diabetic screening or monitoring should be individually read as being used in the method described below. Further, the wellness screening intervention service shall be described below as having the following screening parameters (X): patient blood pressure, patient total cholesterol measurement, patient HDL cholesterol measurement, patient LDL cholesterol measurement, patient triglycerides measurement, patient blood glucose measurement, patient height, patient weight, patient waist measurement. However, these screening parameters are again only for the purpose of example and other screening parameters for wellness screenings or any other intervention service may be requested, received, stored, and transmitted in the manner described hereinbelow.

In step 461, counter variable X is set equal to one. In one example embodiment, counter variable X represents the screening parameters to obtain from the patient for the identified intervention service being provided to the patient. The eligibility services module 148 or another portion of the service provider computer 104 selects the first screening parameter for the identified intervention service in step 462. For example, the eligibility services module 148 may access the intervention parameter files 154 and identify the record associated with the wellness screening, the identified intervention service, based on the destination identifier in the prescription claim transaction 306. The module 148 or another portion of the service provider computer 104 can identify the reject code and/or reject message for the first screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the first screening parameter for the wellness screening is the patient's blood pressure and the reject message can state:

Wellness Screening Documentation: Enter Blood Pressure measurement (Format=SSS/DDD) in the Intermediary Authorization ID field and re-submit. Await request for Total Cholesterol measurement value.

In step 464, the eligibility services module 148 or another portion of the service provider computer 104 can generate a reject response 308(1) to the prescription claim transaction 306. The eligibility services module 148 or another portion of the service provider computer can insert the reject code for the first screening parameter into the response field of the reject response 308(1) and can insert the reject message for the first screening parameter into a predetermined text field of the reject response in step 465. The service provider computer 104 can transmit the reject response 308(1), including the screening parameter reject code and reject message, to the pharmacy computer 106 via, for example, the network 110 in step 466.

In step 467, the pharmacy computer 106 receives the reject response 308(1), including the request for the first screening parameter, via the reject code and/or reject message. In step 468, the pharmacist or other pharmacy employee obtains the first screening parameter from the patient. In the present example, the pharmacy may take the blood pressure of the patient and insert the results of the blood pressure check into a predetermined field of a resubmitted prescription claim transaction 310(1 . . . n). In one example, the predetermined field is the Intermediary Authorization ID field of the resubmitted prescription claim transaction 310(1). In step 469, the pharmacy computer 106 transmits the resubmitted prescription claim transaction 310(1) containing the first screening parameter for the patient to the service provider computer 106 via, for example, the network 110. In one example embodiment, the resubmitted prescription claim transaction 310(1) may include one or more of the following information described above with regard to the prescription claim transaction 302. The service provider computer 104 receives the resubmitted prescription claim transaction 310(1) in step 470.

In step 471, the eligibility services module 148 or another portion of the service provider computer 104 parses the resubmitted prescription claim transaction 310(1) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(1) to determine if screening parameter data for screening parameter X, in this case the first parameter, is included in the predetermined field of the resubmitted prescription claim transaction 310(1). In step 473, an inquiry is conducted to determine if the predetermined field contains the screening parameter data for the first screening parameter. In one example embodiment, the determination can be made by the eligibility services module 148 or another portion of the service provider computer 104. If the resubmitted prescription claim transaction 310(1) does not include the first screening parameter, the NO branch is followed to step 486 of FIG. 4C. Otherwise, the YES branch is followed to step 474, where the eligibility services module 148 or another portion of the service provider computer 104 identifies the screening parameter data for the first screening parameter, for example, the patient blood pressure, in the resubmitted prescription claim transaction 310(1). The screening parameter data for the first screening parameter, for example the patient blood pressure, can be stored in memory 132 and/or in a file of the collected patient parameter files 156 for the patient identified in the transaction 310(1) by the eligibility services module 148 or another portion of the service provider computer 104 in step 475.

In addition, in certain example embodiments, either prior to or after storing the screening parameter data for the first screening parameter, the eligibility services module 148 or another portion of the service provider computer 104 can compare the received screening parameter data to a set of norms (e.g., minimum, maximum, normal responses (e.g., yes/no)) to validate that the received screening parameter data is valid. For example, with regard to blood pressure, the eligibility services module 148 can compare the received systolic and diastolic portions of the blood pressure data to pre-set minimum and/or maximum levels in an effort to verify that received blood pressure data is valid. For example, if the systolic portion of the received blood pressure data is 1000, this could be compared to the pre-set minimum and maximum values of expected values for this type of data. If the received data falls outside of the pre-set range or does not match a normal response (e.g., yes/no), then the eligibility services module 148 may determine that the received screening parameter data value is not valid. In response, the eligibility services module 148 may generate a reject response 308(1 . . . n) to the resubmitted prescription claim transaction 310(1 . . . n). The eligibility services module 148 may further insert a message into the reject response informing that the received screening parameter data does not appear to be valid and requesting verification, which can be completed by the pharmacy resubmitting the resubmitted prescription claim transaction 310(1 . . . n). The eligibility services module 148 or another portion of the service provider computer 104 may then transmit the reject response 308(1 . . . n) and request for validation of the screening parameter data to the pharmacy computer 106 via the network 110. While this optional validation step will not be described below for each screening parameter discussed, the same or similar data validity verification process is anticipated as being conducted for all or at least a portion of received parameter data discussed below. For each, a preset minimum and/or maximum and/or normal response may be stored in, for example, the database 128 or memory 132 and can be retrieved and used for comparison against the received parameter data to verify that the received parameter data is valid.

In step 476, an inquiry is conducted to determine if there is another screening parameter X for the patient to request from the pharmacy computer. In one example embodiment, the determination can be made by the eligibility services module 148 or another portion of the service provider computer. For example, the module 148 can evaluate, based on the destination identifier of the resubmitted transaction 310(1) identifying the intervention service being provided, the corresponding listing of parameters to request in the matching file in the intervention parameter files 154. If no additional parameters need to be requested for the patient under the particular intervention service, the NO branch is followed to step 478 of FIG. 4C. If one or more additional parameters for the patient still need to be collected, then the YES branch is followed to step 477. As an example, the following will describe requesting, receiving and storing the eight additional parameters to be collected under the exemplary wellness screening intervention service. In step 477, the counter variable is incremented by one and the process returns to step 462.

The eligibility services module 148 or another portion of the service provider computer 104 selects the second screening parameter for the identified intervention service in step 462 in substantially the same manner as described above. The module 148 or another portion of the service provider computer 104 can identify the reject code and/or reject message for the second screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the second screening parameter for the wellness screening is the patient's total cholesterol measurement and the reject message can state:

Wellness Screening Documentation: Enter Total Cholesterol measurement in the Intermediary Authorization ID field and re-submit. Await request for HDL Cholesterol measurement value.

In step 464, the eligibility services module 148 or another portion of the service provider computer 104 can generate a reject response 308(2) to the resubmitted prescription claim transaction 310(1). The eligibility services module 148 or another portion of the service provider computer 104 can insert the reject code for the second screening parameter into the response field of the reject response 308(2) and can insert the reject message for the second screening parameter into a predetermined text field of the reject response 308(2) in step 465. The service provider computer 104 can transmit the reject response 308(2), including the screening parameter reject code and reject message, to the pharmacy computer 106 via, for example, the network 110 in step 466.

In step 467, the pharmacy computer 106 receives the reject response 308(2), including the request for the second screening parameter, via the reject code and/or reject message. In step 468, the pharmacist or other pharmacy employee obtains the second screening parameter, for example the patient's total cholesterol measurement, from the patient. The pharmacy may determine the patient's total cholesterol measurement and insert the results of the total cholesterol measurement into the Intermediary Authorization ID field of a resubmitted prescription claim transaction 310(2). In step 469, the pharmacy computer 106 transmits the resubmitted prescription claim transaction 310(2) containing the second screening parameter data for the patient to the service provider computer 106 via, for example, the network 110. The service provider computer 104 receives the resubmitted prescription claim transaction 310(2) in step 470.

In step 471, the eligibility services module 148 or another portion of the service provider computer 104 parses the resubmitted prescription claim transaction 310(2) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(2) to determine if screening parameter data for the second parameter is included in the predetermined field of the resubmitted prescription claim transaction 310(2). In step 473, an inquiry is conducted to determine if the predetermined field contains the screening parameter data for the second screening parameter in a manner substantially the same as described above. If the resubmitted prescription claim transaction 310(2) does not include the second screening parameter, the NO branch is followed to step 486 of FIG. 4C. Otherwise, the YES branch is followed to step 474, where the eligibility services module 148 or another portion of the service provider computer 104 identifies the screening parameter data for the second screening parameter, for example, the patient's total cholesterol measurement, in the resubmitted prescription claim transaction 310(2). The second screening parameter data for the patient can be stored in memory 132 and/or in a file of the collected patient parameter files 156 for the patient identified in the transaction 310(2) in step 475.

In step 476, an inquiry is conducted to determine if there is another screening parameter X for the patient to request from the pharmacy computer 106. In one example embodiment, the determination can be made by the eligibility services module 148 or another portion of the service provider computer 104 in substantially the same manner as described above. If no additional parameters need to be requested for the patient under the particular intervention service, the NO branch is followed to step 478 of FIG. 4C. Otherwise, the YES branch is followed to step 477. In step 477, the counter variable is incremented by one and the process returns to step 462.

The eligibility services module 148 or another portion of the service provider computer 104 selects the third screening parameter for the wellness screening intervention service in step 462 in substantially the same manner as described above. The module 148 or another portion of the service provider computer 104 can identify the reject code and/or reject message for the third screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the third screening parameter for the wellness screening is the patient's high-density lipoproteins (HDL) cholesterol measurement and the reject message can state:

Wellness Screening Documentation: Enter HDL Cholesterol measurement in the Intermediary Authorization ID field and re-submit. Await request for LDL Cholesterol measurement value.

In step 464, the eligibility services module 148 or another portion of the service provider computer 104 can generate a reject response 308(3) to the resubmitted prescription claim transaction 310(2). The eligibility services module 148 or another portion of the service provider computer 104 can insert the reject code for the third screening parameter into the response field of the reject response 308(3) and can insert the reject message for the third screening parameter into a predetermined text field of the reject response 308(3) in step 465. The service provider computer 104 can transmit the reject response 308(3), including the third screening parameter reject code and reject message, to the pharmacy computer 106 via, for example, the network 110 in step 466.

In step 467, the pharmacy computer 106 receives the reject response 308(3), including the request for the third screening parameter, via the reject code and/or reject message. In step 468, the pharmacist or other pharmacy employee obtains the third screening parameter, for example the patient's HDL cholesterol measurement, from the patient. The pharmacy may determine the patient's HDL cholesterol measurement and insert the results of the HDL cholesterol measurement into the Intermediary Authorization ID field of a resubmitted prescription claim transaction 310(3). In step 469, the pharmacy computer 106 transmits the resubmitted prescription claim transaction 310(3) containing the third screening parameter data for the patient to the service provider computer 106 via, for example, the network 110. The service provider computer 104 receives the resubmitted prescription claim transaction 310(3) in step 470.

In step 471, the eligibility services module 148 or another portion of the service provider computer 104 parses the resubmitted prescription claim transaction 310(3) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(3) to determine if screening parameter data for the third parameter is included in the predetermined field of the resubmitted prescription claim transaction 310(3). In step 473, an inquiry is conducted to determine if the predetermined field contains the screening parameter data for the third screening parameter in a manner substantially the same as described above. If the resubmitted prescription claim transaction 310(3) does not include the third screening parameter, the NO branch is followed to step 486 of FIG. 4C. Otherwise, the YES branch is followed to step 474, where the eligibility services module 148 or another portion of the service provider computer 104 identifies the screening parameter data for the third screening parameter, for example the patient's HDL cholesterol measurement, in the resubmitted prescription claim transaction 310(3). The third screening parameter data for the patient can be stored in memory 132 and/or in a file of the collected patient parameter files 156 for the patient identified in the transaction 310(3) in step 475.

In step 476, an inquiry is conducted to determine if there is another screening parameter X for the patient to request from the pharmacy computer 106. In one example embodiment, the determination can be made by the eligibility services module 148 or another portion of the service provider computer 104 in substantially the same manner as described above. If no additional parameters need to be requested for the patient under the particular intervention service, the NO branch is followed to step 478 of FIG. 4C. Otherwise, the YES branch is followed to step 477. In step 477, the counter variable is incremented by one and the process returns to step 462.

The eligibility services module 148 or another portion of the service provider computer 104 selects the fourth screening parameter for the wellness screening intervention service in step 462 in substantially the same manner as described above. The module 148 or another portion of the service provider computer 104 can identify the reject code and/or reject message for the fourth screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the fourth screening parameter for the wellness screening intervention service is the patient's low-density lipoproteins (LDL) cholesterol measurement and the reject message can state:

Wellness Screening Documentation: Enter LDL Cholesterol measurement in the Intermediary Authorization ID field and re-submit. Await request for Triglycerides measurement value.

In step 464, the eligibility services module 148 or another portion of the service provider computer 104 can generate a reject response 308(4) to the resubmitted prescription claim transaction 310(3). The eligibility services module 148 or another portion of the service provider computer 104 can insert the reject code for the fourth screening parameter into the response field of the reject response 308(4) and can insert the reject message for the fourth screening parameter into a predetermined text field of the reject response 308(4) in step 465. The service provider computer 104 can transmit the reject response 308(4), including the fourth screening parameter reject code and reject message, to the pharmacy computer 106 via, for example, the network 110 in step 466.

In step 467, the pharmacy computer 106 receives the reject response 308(4), including the request for the fourth screening parameter, via the reject code and/or reject message. In step 468, the pharmacist or other pharmacy employee obtains the fourth screening parameter, for example the patient's LDL cholesterol measurement, from the patient. The pharmacy may determine the patient's LDL cholesterol measurement and insert the results of the LDL cholesterol measurement into the Intermediary Authorization ID field of a resubmitted prescription claim transaction 310(4). In step 469, the pharmacy computer 106 transmits the resubmitted prescription claim transaction 310(4) containing the fourth screening parameter data for the patient to the service provider computer 106 via, for example, the network 110. The service provider computer 104 receives the resubmitted prescription claim transaction 310(4) in step 470.

In step 471, the eligibility services module 148 or another portion of the service provider computer 104 parses the resubmitted prescription claim transaction 310(4) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(4) to determine if screening parameter data for the fourth parameter is included in the predetermined field of the resubmitted prescription claim transaction 310(4). In step 473, an inquiry is conducted to determine if the predetermined field contains the screening parameter data for the fourth screening parameter in a manner substantially the same as described above. If the resubmitted prescription claim transaction 310(4) does not include the fourth screening parameter, the NO branch is followed to step 486 of FIG. 4C. Otherwise, the YES branch is followed to step 474, where the eligibility services module 148 or another portion of the service provider computer 104 identifies the screening parameter data for the fourth screening parameter, for example the patient's LDL cholesterol measurement, in the resubmitted prescription claim transaction 310(4). The fourth screening parameter data for the patient can be stored in memory 132 and/or in a file of the collected patient parameter files 156 for the patient identified in the transaction 310(4) in step 475.

In step 476, an inquiry is conducted to determine if there is another screening parameter X for the patient to request from the pharmacy computer 106. In one example embodiment, the determination can be made by the eligibility services module 148 or another portion of the service provider computer 104 in substantially the same manner as described above. If no additional parameters need to be requested for the patient under the particular intervention service, the NO branch is followed to step 478 of FIG. 4C. Otherwise, the YES branch is followed to step 477. In step 477, the counter variable is incremented by one and the process returns to step 462.

The eligibility services module 148 or another portion of the service provider computer 104 selects the fifth screening parameter for the wellness screening intervention service in step 462 in substantially the same manner as described above. The module 148 or another portion of the service provider computer 104 can identify the reject code and/or reject message for the fifth screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the fifth screening parameter for the wellness screening intervention service is the patient's triglycerides measurement and the reject message can state:

Wellness Screening Documentation: Enter Triglycerides measurement in the Intermediary Authorization ID field and re-submit. Await request for Blood Glucose measurement value.

In step 464, the eligibility services module 148 or another portion of the service provider computer 104 can generate a reject response 308(5) to the resubmitted prescription claim transaction 310(4). The eligibility services module 148 or another portion of the service provider computer 104 can insert the reject code for the fifth screening parameter into the response field of the reject response 308(5) and can insert the reject message for the fifth screening parameter into a predetermined text field of the reject response 308(5) in step 465. The service provider computer 104 can transmit the reject response 308(5), including the fifth screening parameter reject code and reject message, to the pharmacy computer 106 via, for example, the network 110 in step 466.

In step 467, the pharmacy computer 106 receives the reject response 308(5), including the request for the fifth screening parameter, via the reject code and/or reject message. In step 468, the pharmacist or other pharmacy employee obtains the fifth screening parameter, for example the patient's triglycerides measurement, from the patient. The pharmacy may determine the patient's triglycerides measurement and insert the results of the triglycerides measurement into the Intermediary Authorization ID field of a resubmitted prescription claim transaction 310(5). In step 469, the pharmacy computer 106 transmits the resubmitted prescription claim transaction 310(5) containing the fifth screening parameter data for the patient to the service provider computer 106 via, for example, the network 110. The service provider computer 104 receives the resubmitted prescription claim transaction 310(5) in step 470.

In step 471, the eligibility services module 148 or another portion of the service provider computer 104 parses the resubmitted prescription claim transaction 310(5) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(5) to determine if screening parameter data for the fifth parameter is included in the predetermined field of the resubmitted prescription claim transaction 310(5). In step 473, an inquiry is conducted to determine if the predetermined field contains the screening parameter data for the fifth screening parameter in a manner substantially the same as described above. If the resubmitted prescription claim transaction 310(5) does not include the fifth screening parameter, the NO branch is followed to step 486 of FIG. 4C. Otherwise, the YES branch is followed to step 474, where the eligibility services module 148 or another portion of the service provider computer 104 identifies the screening parameter data for the fifth screening parameter, for example the patient's triglycerides measurement, in the resubmitted prescription claim transaction 310(5). The fifth screening parameter data for the patient can be stored in memory 132 and/or in a file of the collected patient parameter files 156 for the patient identified in the transaction 310(5) in step 475.

In step 476, an inquiry is conducted to determine if there is another screening parameter X for the patient to request from the pharmacy computer 106. In one example embodiment, the determination can be made by the eligibility services module 148 or another portion of the service provider computer 104 in substantially the same manner as described above. If no additional parameters need to be requested for the patient under the particular intervention service, the NO branch is followed to step 478 of FIG. 4C. Otherwise, the YES branch is followed to step 477. In step 477, the counter variable is incremented by one and the process returns to step 462.

The eligibility services module 148 or another portion of the service provider computer 104 selects the sixth screening parameter for the wellness screening intervention service in step 462 in substantially the same manner as described above. The module 148 or another portion of the service provider computer 104 can identify the reject code and/or reject message for the sixth screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the sixth screening parameter for the wellness screening intervention service is the patient's blood glucose measurement and the reject message can state:

Wellness Screening Documentation: Enter Blood Glucose measurement in the Intermediary Authorization ID field and re-submit. Await request for Height measurement value.

In step 464, the eligibility services module 148 or another portion of the service provider computer 104 can generate a reject response 308(6) to the resubmitted prescription claim transaction 310(5). The eligibility services module 148 or another portion of the service provider computer 104 can insert the reject code for the sixth screening parameter into the response field of the reject response 308(6) and can insert the reject message for the sixth screening parameter into a predetermined text field of the reject response 308(6) in step 465. The service provider computer 104 can transmit the reject response 308(6), including the sixth screening parameter reject code and reject message, to the pharmacy computer 106 via, for example, the network 110 in step 466.

In step 467, the pharmacy computer 106 receives the reject response 308(6), including the request for the sixth screening parameter, via the reject code and/or reject message. In step 468, the pharmacist or other pharmacy employee obtains the sixth screening parameter, for example the patient's blood glucose measurement, from the patient. The pharmacy may determine the patient's blood glucose measurement and insert the results of the blood glucose measurement into the Intermediary Authorization ID field of a resubmitted prescription claim transaction 310(6). In step 469, the pharmacy computer 106 transmits the resubmitted prescription claim transaction 310(6) containing the sixth screening parameter data for the patient to the service provider computer 106 via, for example, the network 110. The service provider computer 104 receives the resubmitted prescription claim transaction 310(6) in step 470.

In step 471, the eligibility services module 148 or another portion of the service provider computer 104 parses the resubmitted prescription claim transaction 310(6) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(6) to determine if screening parameter data for the sixth parameter is included in the predetermined field of the resubmitted prescription claim transaction 310(6). In step 473, an inquiry is conducted to determine if the predetermined field contains the screening parameter data for the sixth screening parameter in a manner substantially the same as described above. If the resubmitted prescription claim transaction 310(6) does not include the sixth screening parameter, the NO branch is followed to step 486 of FIG. 4C. Otherwise, the YES branch is followed to step 474, where the eligibility services module 148 or another portion of the service provider computer 104 identifies the screening parameter data for the sixth screening parameter, for example the patient's blood glucose measurement, in the resubmitted prescription claim transaction 310(6). The sixth screening parameter data for the patient can be stored in memory 132 and/or in a file of the collected patient parameter files 156 for the patient identified in the transaction 310(6) in step 475.

In step 476, an inquiry is conducted to determine if there is another screening parameter X for the patient to request from the pharmacy computer 106. In one example embodiment, the determination can be made by the eligibility services module 148 or another portion of the service provider computer 104 in substantially the same manner as described above. If no additional parameters need to be requested for the patient under the particular intervention service, the NO branch is followed to step 478 of FIG. 4C. Otherwise, the YES branch is followed to step 477. In step 477, the counter variable is incremented by one and the process returns to step 462.

The eligibility services module 148 or another portion of the service provider computer 104 selects the seventh screening parameter for the wellness screening intervention service in step 462 in substantially the same manner as described above. The module 148 or another portion of the service provider computer 104 can identify the reject code and/or reject message for the seventh screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the seventh screening parameter for the wellness screening intervention service is the patient's height measurement and the reject message can state:

Wellness Screening Documentation: Enter Patient Height measurement (inches) in the Intermediary Authorization ID field and re-submit. Await request for Patient Weight measurement value.

In step 464, the eligibility services module 148 or another portion of the service provider computer 104 can generate a reject response 308(7) to the resubmitted prescription claim transaction 310(6). The eligibility services module 148 or another portion of the service provider computer 104 can insert the reject code for the seventh screening parameter into the response field of the reject response 308(7) and can insert the reject message for the seventh screening parameter into a predetermined text field of the reject response 308(7) in step 465. The service provider computer 104 can transmit the reject response 308(7), including the seventh screening parameter reject code and reject message, to the pharmacy computer 106 via, for example, the network 110 in step 466.

In step 467, the pharmacy computer 106 receives the reject response 308(7), including the request for the seventh screening parameter, via the reject code and/or reject message. In step 468, the pharmacist or other pharmacy employee obtains the seventh screening parameter, for example the patient's height measurement, from the patient. The pharmacy may determine the patient's height measurement and insert the results of the height measurement into the Intermediary Authorization ID field of a resubmitted prescription claim transaction 310(7). In step 469, the pharmacy computer 106 transmits the resubmitted prescription claim transaction 310(7) containing the seventh screening parameter data for the patient to the service provider computer 106 via, for example, the network 110. The service provider computer 104 receives the resubmitted prescription claim transaction 310(7) in step 470.

In step 471, the eligibility services module 148 or another portion of the service provider computer 104 parses the resubmitted prescription claim transaction 310(7) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(7) to determine if screening parameter data for the seventh parameter is included in the predetermined field of the resubmitted prescription claim transaction 310(7). In step 473, an inquiry is conducted to determine if the predetermined field contains the screening parameter data for the seventh screening parameter in a manner substantially the same as described above. If the resubmitted prescription claim transaction 310(7) does not include the seventh screening parameter, the NO branch is followed to step 486 of FIG. 4C. Otherwise, the YES branch is followed to step 474, where the eligibility services module 148 or another portion of the service provider computer 104 identifies the screening parameter data for the seventh screening parameter, for example the patient's height measurement, in the resubmitted prescription claim transaction 310(7). The seventh screening parameter data for the patient can be stored in memory 132 and/or in a file of the collected patient parameter files 156 for the patient identified in the transaction 310(7) in step 475.

In step 476, an inquiry is conducted to determine if there is another screening parameter X for the patient to request from the pharmacy computer 106. In one example embodiment, the determination can be made by the eligibility services module 148 or another portion of the service provider computer 104 in substantially the same manner as described above. If no additional parameters need to be requested for the patient under the particular intervention service, the NO branch is followed to step 478 of FIG. 4C. Otherwise, the YES branch is followed to step 477. In step 477, the counter variable is incremented by one and the process returns to step 462.

The eligibility services module 148 or another portion of the service provider computer 104 selects the eighth screening parameter for the wellness screening intervention service in step 462 in substantially the same manner as described above. The module 148 or another portion of the service provider computer 104 can identify the reject code and/or reject message for the eighth screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the eighth screening parameter for the wellness screening intervention service is the patient's weight and the reject message can state:

Wellness Screening Documentation: Enter Patient Weight measurement (lbs.) in the Intermediary Authorization ID field and re-submit. Await request for Waist Measurement value.

In step 464, the eligibility services module 148 or another portion of the service provider computer 104 can generate a reject response 308(8) to the resubmitted prescription claim transaction 310(7). The eligibility services module 148 or another portion of the service provider computer 104 can insert the reject code for the eighth screening parameter into the response field of the reject response 308(8) and can insert the reject message for the eighth screening parameter into a predetermined text field of the reject response 308(8) in step 465. The service provider computer 104 can transmit the reject response 308(8), including the eighth screening parameter reject code and reject message, to the pharmacy computer 106 via, for example, the network 110 in step 466.

In step 467, the pharmacy computer 106 receives the reject response 308(8), including the request for the eighth screening parameter, via the reject code and/or reject message. In step 468, the pharmacist or other pharmacy employee obtains the eighth screening parameter, for example the patient's weight, from the patient. The pharmacy may determine the patient's weight and insert the results of the weight measurement into the Intermediary Authorization ID field of a resubmitted prescription claim transaction 310(8). In step 469, the pharmacy computer 106 transmits the resubmitted prescription claim transaction 310(8) containing the eighth screening parameter data for the patient to the service provider computer 106 via, for example, the network 110. The service provider computer 104 receives the resubmitted prescription claim transaction 310(8) in step 470.

In step 471, the eligibility services module 148 or another portion of the service provider computer 104 parses the resubmitted prescription claim transaction 310(8) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(8) to determine if screening parameter data for the eighth parameter is included in the predetermined field of the resubmitted prescription claim transaction 310(8). In step 473, an inquiry is conducted to determine if the predetermined field contains the screening parameter data for the eighth screening parameter in a manner substantially the same as described above. If the resubmitted prescription claim transaction 310(8) does not include the eighth screening parameter, the NO branch is followed to step 486 of FIG. 4C. Otherwise, the YES branch is followed to step 474, where the eligibility services module 148 or another portion of the service provider computer 104 identifies the screening parameter data for the eighth screening parameter, for example the patient's weight, in the resubmitted prescription claim transaction 310(8). The eighth screening parameter data for the patient can be stored in memory 132 and/or in a file of the collected patient parameter files 156 for the patient identified in the transaction 310(8) in step 475.

In step 476, an inquiry is conducted to determine if there is another screening parameter X for the patient to request from the pharmacy computer 106. In one example embodiment, the determination can be made by the eligibility services module 148 or another portion of the service provider computer 104 in substantially the same manner as described above. If no additional parameters need to be requested for the patient under the particular intervention service, the NO branch is followed to step 478 of FIG. 4C. Otherwise, the YES branch is followed to step 477. In step 477, the counter variable is incremented by one and the process returns to step 462.

The eligibility services module 148 or another portion of the service provider computer 104 selects the ninth screening parameter for the wellness screening intervention service in step 462 in substantially the same manner as described above. The module 148 or another portion of the service provider computer 104 can identify the reject code and/or reject message for the ninth screening parameter in step 463. In one example embodiment, the reject code is a unique reject code for the particular screening parameter (X) and can designate that the particular screening parameter is to be collected from the patient as part of the wellness screening. Similarly, the reject message may provide instructions to the pharmacist or other pharmacy employee as to what screening parameter is to be obtained from the patient. In one example embodiment, the ninth screening parameter for the wellness screening intervention service is the patient's waist measurement and the reject message can state:

Wellness Screening Documentation: Enter Patient Weight measurement (inches) in the Intermediary Authorization ID field and re-submit to complete screening documentation.

In step 464, the eligibility services module 148 or another portion of the service provider computer 104 can generate a reject response 308(9) to the resubmitted prescription claim transaction 310(8). The eligibility services module 148 or another portion of the service provider computer 104 can insert the reject code for the ninth screening parameter into the response field of the reject response 308(9) and can insert the reject message for the ninth screening parameter into a predetermined text field of the reject response 308(9) in step 465. The service provider computer 104 can transmit the reject response 308(9), including the ninth screening parameter reject code and reject message, to the pharmacy computer 106 via, for example, the network 110 in step 466.

In step 467, the pharmacy computer 106 receives the reject response 308(9), including the request for the ninth screening parameter, via the reject code and/or reject message. In step 468, the pharmacist or other pharmacy employee obtains the ninth screening parameter, for example the patient's waist measurement, from the patient. The pharmacy may determine the patient's waist measurement and insert the results of the waist measurement into the Intermediary Authorization ID field of a resubmitted prescription claim transaction 310(9). In step 469, the pharmacy computer 106 transmits the resubmitted prescription claim transaction 310(9) containing the ninth screening parameter data for the patient to the service provider computer 106 via, for example, the network 110. The service provider computer 104 receives the resubmitted prescription claim transaction 310(9) in step 470.

In step 471, the eligibility services module 148 or another portion of the service provider computer 104 parses the resubmitted prescription claim transaction 310(9) to identify the pharmacy identifier (e.g., pharmacy name, NPI, chain identifier, etc.) and one or more patient identifiers and compares the pharmacy identifier and patient identifiers to a table, schedule, or listing of pharmacy identifiers for pharmacies that have initiated an intervention service documentation for the identified patient. Based on a match, the module 148 can determine that the pharmacy is providing an intervention service documentation, such as the wellness screening, for the identified patient.

In step 472, the eligibility services module 148 or another portion of the service provider computer 104 can parse the resubmitted prescription claim transaction 310(9) to determine if screening parameter data for the ninth parameter is included in the predetermined field of the resubmitted prescription claim transaction 310(9). In step 473, an inquiry is conducted to determine if the predetermined field contains the screening parameter data for the ninth screening parameter in a manner substantially the same as described above. If the resubmitted prescription claim transaction 310(9) does not include the ninth screening parameter, the NO branch is followed to step 486 of FIG. 4C. Otherwise, the YES branch is followed to step 474, where the eligibility services module 148 or another portion of the service provider computer 104 identifies the screening parameter data for the ninth screening parameter, for example the patient's waist measurement, in the resubmitted prescription claim transaction 310(9). The ninth screening parameter data for the patient can be stored in memory 132 and/or in a file of the collected patient parameter files 156 for the patient identified in the transaction 310(9) in step 475.

In step 476, an inquiry is conducted to determine if there is another screening parameter X for the patient to request from the pharmacy computer 106. In one example embodiment, the determination can be made by the eligibility services module 148 or another portion of the service provider computer 104 in substantially the same manner as described above. If no additional parameters need to be requested for the patient under the particular intervention service, the NO branch is followed to step 478 of FIG. 4C. Otherwise, the YES branch is followed to step 477. In step 477, the counter variable is incremented by one and the process returns to step 462.

While the example intervention service documentation shown above describes the collection of nine unique screening parameters in nine separate round trips of a transaction/response, those of ordinary skill will recognize that fewer or greater numbers of screening parameters may be collected and that the number and types of screening parameters collected can be based on the intervention service being provided to the patient. In one example embodiment, other parameters that may be collected include, but are not limited to respiratory volume (e.g., tidal volume—the lung volume representing the normal volume of air displaced between normal inhalation and exhalation when extra effort is not applied), oxygen levels, a code providing an indication of why the intervention service was declined by the patient, was not provided to the patient, or was not applicable to the particular patient.

In step 478, the eligibility services module 148 or another portion of the service provider computer 104 determines that all of the screening parameter data for the identified intervention service has been received from the pharmacy computer 106. For example, the module 148 may determine, based on a review of the corresponding file in the intervention parameter files 154 that all parameter data has been collected for the identified intervention service. In step 479, the eligibility services module 148 or another portion of the service provider computer 104 can store an indication that the identified intervention service has been completed for the identified patient. For example, the eligibility services module 148 can access the corresponding file in the intervention notification files 153 from the database 128 for the identified patient and can insert information designating that the particular intervention service has been completed for the patient.

The eligibility services module 148 or another portion of the service provider computer can generate an approval response 312 to the resubmitted prescription claim transaction 310(1 . . . n) in step 480. In one example embodiment, the approval response 312 may include a text field notifying the pharmacy associated with the pharmacy computer 106 that all requirements for the identified intervention service have been completed. In step 481, the service provider computer 104 can transmit the approval response 312 to the pharmacy computer 104 via, for example, the network 110. In step 482, the pharmacy computer 106 can receive the approval response 312. The process 400 may continue to the END step.

Returning to step 479, the process may also continue to step 483, where the eligibility services module 148 or another portion of the service provider computer can generate a transmittal of the received and stored intervention service parameter data for the patient. In one example embodiment, the intervention service parameter data for the patient can be collected with other parameter data for other patients for the same or other intervention services and can be sent in a batch format from the service provider computer to the claims processor computer 108. In an alternative embodiment, the eligibility services module 148 or another portion of the service provider computer 104 can generate a single billing transaction request 314 that includes the one or more patient identifiers for the patient identified in the resubmitted prescription claim transaction 310(1 . . . n), the destination identifier designating the intervention service provided to that patient, and each of the intervention service parameter data collected from the patient and stored from the resubmitted prescription claim transactions 310(1 . . . n) during the intervention service. In one example embodiment, the single billing transaction request 314 is an NCPDP telecommunication formatted billing transaction request 314 that can be in the following format:

i. Header:
1. Segment ID: "HDR"
2. File Name: Wellness Screening—Pharmacy Activity Report
3. Sponsor ID: "VARCHAR2(10)
4. Sponsor Name: "Claims Processor Name or Identifier"
5. Date/Time: "MMddccyyHHmmss"
6. Total Notifications: "NN,NNN"
7. Total Billing/Documentation Requests: "NN,NNN"
8. Ratio (Approved Request/Notifications X 100): "X %"

ii. Transaction:
1. Segment ID: - - - "DTL
2. BIN Number: - - - 9(6)
3. Processor Control Number: - - - X(10)
4. Transaction Code: - - - S1 or S2
5. Service Provider ID: - - - X(15)
6. Date of Service: - - - 9(8)
7. Cardholder ID: - - - X(20)
8. Rx/Service Reference # Qualifier: - - - "1" or "2"
9. Rx/Service Reference #: - - - 9(12)
10. Professional Service Code - - - "PT" (Perform Lab Test)
11. Clinical Information Counter - - - "1"

12. Measurement Date - - - 9(8) CCYYMMDD
13. Measure Time - - - 9(4) HHMM
14. Measurement Dimension - - - "01" (Blood Pressure)
15. Measurement Unit - - - "10" (mmHg)
16. Measurement Value - - - 9(18)
17. Clinical Information Counter - - - "2"
18. Measurement Date - - - 9(8) CCYYMMDD
19. Measure Time - - - 9(4) HHMM
20. Measurement Dimension - - - "18" (Total Cholesterol)
21. Measurement Unit - - - "08" (mg/dl)
22. Measurement Value - - - 9(18)
23. Clinical Information Counter - - - "3"
24. Measurement Date - - - 9(8) CCYYMMDD
25. Measure Time - - - 9(4) HHMM
26. Measurement Dimension - - - "20" (HDL Cholesterol)
27. Measurement Unit - - - "08" (mg/dl)
28. Measurement Value - - - 9(18)
29. Clinical Information Counter - - - "4"
30. Measurement Date - - - 9(8) CCYYMMDD
31. Measure Time - - - 9(4) HHMM
32. Measurement Dimension - - - "19" (LDL Cholesterol)
33. Measurement Unit - - - "08" (mg/dl)
34. Measurement Value - - - 9(18)
35. Clinical Information Counter - - - "5"
36. Measurement Date - - - 9(8) CCYYMMDD
37. Measure Time - - - 9(4) HHMM
38. Measurement Dimension - - - "21" (Triglycerides)
39. Measurement Unit - - - "08" (mg/dl)
40. Measurement Value - - - 9(18)
41. Clinical Information Counter - - - "6"
42. Measurement Date - - - 9(8) CCYYMMDD
43. Measure Time - - - 9(4) HHMM
44. Measurement Dimension - - - "02" (Blood Glucose)
45. Measurement Unit - - - "08" (mg/dl)
46. Measurement Value - - - 9(18)
47. Clinical Information Counter - - - "7"
48. Measurement Date - - - 9(8) CCYYMMDD
49. Measure Time - - - 9(4) HHMM
50. Measurement Dimension - - - "16" (Patient Height)
51. Measurement Unit - - - "01" (Inches)
52. Measurement Value - - - 9(18)
53. Clinical Information Counter - - - "8"
54. Measurement Date - - - 9(8) CCYYMMDD
55. Measure Time - - - 9(4) HHMM
56. Measurement Dimension - - - "14" (Patient Weight)
57. Measurement Unit - - - "03" (lbs)
58. Measurement Value - - - 9(18)
59. Clinical Information Counter - - - "9"
60. Measurement Date - - - 9(8) CCYYMMDD
61. Measure Time - - - 9(4) HHMM
62. Measurement Dimension - - - "99" (Patient Waist Size)
63. Measurement Unit - - - "01" (Inches)
64. Measurement Value - - - 9(18)

In step 484, the service provider computer 104 can transmit the single billing transaction request 314, including all of the collected parameters during an intervention service for the patient, to the claims processor computer 108 via the network 110. The claims processor computer 108 can receive the billing transaction request and can store the screening parameter data included in the billing transaction request 314 in step 485. The process can proceed to the END step.

Returning to the inquiries of steps 450, 454, 458, and 473, the NO branch of each is followed to step 486. In step 486, the eligibility services module 148 or another portion of the service provider computer 104 can parse the prescription claim transaction 306 or resubmitted prescription claim transaction 310(1 . . . n) to identify a reason code included in a predetermined field of the transaction 306, 310(1 . . . n). In one example embodiment, the reason code can represent a reason that the intervention service identified for the patient in the reject response 304 was not completed (either in whole or in part). The eligibility services module 148 or another portion of the service provider computer 104 can store the identified reason code signifying the reason an intervention was not completed in step 487. For example, the reason code may be stored in the database 128, such as in the file associated with the patient in the patient eligibility information files 150 or the collected patient parameter files 156, or in memory 132 by the eligibility services module 148. In one example embodiment, multiple reason codes representing multiple reasons may be presented in the transaction 306, 310(1 . . . n).

In step 488, the eligibility services module 148 or another portion of the service provider computer 104 can create a modified prescription claim transaction 316 from the prescription claim transaction 306 or resubmitted prescription claim transaction 310(1 . . . n) by removing the identified one or more reason codes from the transaction 306, 310(1 . . . n). In step 489, the service provider computer 104 can transmit or otherwise send the modified prescription claim transaction 316, via, for example the network 110, to the claims processor computer 108 identified by the destination identifier for adjudication. In step 490, the claims processor computer 108 can receive the modified prescription claim transaction 316 from the service provider computer 104.

The claims processor computer 108 may adjudicate or otherwise process the modified prescription claim transaction 316 in step 491. For example, the claims processor computer 108 may determine benefits coverage for the modified prescription claim transaction 316 according to an adjudication process associated with eligibility, pricing, and/or utilization review. In step 492, the claims processor computer 108 may transmit or otherwise communicate an adjudicated response 318 of the modified prescription claim transaction 316 to the service provider computer 104 via, for example, the network 110. The adjudicated response 318 may include, without limitation, a transaction status indicator indicating whether the modified prescription claim transaction 316 was paid or rejected. In one example embodiment, when the modified prescription claim transaction 316 is paid, the adjudicated response 318 may include a transaction status indicator "P". If, however, the modified prescription claim transaction 316 is rejected, the adjudicated response 318 may include a transaction indicator "R".

In one example, when the adjudicated response 318 includes a transaction status indicator "P", the adjudicated response 318 may also include, without limitation, one or more fields comprising a patient pay amount field (the patient co-pay) populated with a value returned by the claims processor computer 108, an associated quantity dispensed field populated with a submitted quantity to be dispensed on the modified prescription claim transaction 316, and/or a pharmacy name field populated with a short pharmacy name corresponding to the submitted pharmacy identifier on the modified prescription claim transaction 316.

If, on the other hand, the adjudicated response 318 includes the transaction status indicator "R", the adjudicated response 318 may also include, without limitation, one or more fields comprising the patient pay amount field left blank, the associated dispensed quantity field left blank, a reject reason field populated with a reject code (e.g., pricing not available for an identified scenario, reject description, patient not covered, medication not in formulary, or the like), the pharmacy name field is left blank, a reason for service code field populated with a reject error code, and/or a reason for service description field populated with an abbreviated description of the corresponding reason for service code.

In step 493, the service provider computer 104 receives the adjudicated response 318 from the claims processor computer 108. Upon receipt, the service provider computer 104 may determine whether the modified prescription claim transaction 316 was approved for payment or denied/rejected by the claims processor computer 108. In one example, the service provider computer 104 may parse the adjudicated response 318 to identify the transaction status indicator in the response 318. The service provider computer 106 may transmit or otherwise communicate the adjudicated response 318 to the pharmacy computer 106 via, for example, the network 110 in step 494. In step 495, the pharmacy computer can receive the adjudicated response 318. If the adjudicated response 318 is approved/paid, the pharmacy associated with the pharmacy computer 106 may dispense the requested medication, product, or service identified in the prescription claim transaction 306, 310(1 . . . n) to the patient in step 496. If the adjudicated response 318 is a denial/rejection of the modified prescription claim transaction 316, then the pharmacy can inform the patient of the reason for the denial/rejection based on the reject code included in the adjudicated response 318. The process may continue to the END step.

The methods described and shown in FIGS. 2-4C may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 2-4C may be performed.

Accordingly, example embodiments disclosed herein can provide the technical effects of creating a system and methods that provide a way to determine and communicate intervention service opportunities (e.g., wellness screening, blood pressure monitoring, MTM services, immunization messaging, cash prescription monitoring, refill adherence, high-risk medication monitoring, and diabetic screening or monitoring, etc.) that may be available for a patient. Further, the example embodiments disclosed herein can provide the technical effects of creating a system and methods that provide a way to request, obtain, and store patient parameter data collected from a patient during the intervention service opportunity via a sequence of healthcare transaction submissions and responses and collecting and transmitting the patient parameter data to a claims processor computer, as part of the processing of a healthcare transaction.

While certain example embodiments disclosed herein describe the eligibility services module 148 as a processor device separate from the service provider computer 104, in alternate embodiments the eligibility services module 148 or the functions that it completes may be incorporated into the service provider computer 104. In those alternate embodiments and with regard to the methods described above, the steps describing transmitting or receiving between the service provider computer 104 and the eligibility services module 148 may be internal transmissions within the service provider computer or may be omitted altogether. Further, while the exemplary embodiments described herein disclose certain steps occurring at the service provider computer 104 and/or the eligibility services module 148, in alternative embodiments those elements described with reference to FIGS. 1-4C may alternately be completed at the eligibility sponsor computer 102, the pharmacy computer 106, the claims processor computer 108, a combination of those devices, and/or a combination of those devices along with the service provider computer 104. In those alternate embodiments, certain transmission/receiving steps described above with reference to FIGS. 1-4C may be omitted while others may be added, as understood by one of ordinary skill in the art. The intent being that in alternate embodiments, any of the devices/computers discussed in FIG. 1 are capable of completing any or any part of the methods described with reference to FIGS. 2-4C.

Although example embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block diagrams and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, may be implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium (e.g., transitory or non-transitory) produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

That which is claimed is:

1. A computer-implemented method for determining patient intervention services, the method comprising:
   receiving, by one or more service provider computers comprising one or more processors from a pharmacy computer associated with a pharmacy, a healthcare claim transaction comprising a patient identifier identifying a patient and a destination identifier;
   in response to receipt of the healthcare claim transaction, determining whether (1) an intervention service is available for the patient identified by the patient identifier based upon a review of patient eligibility information from a patient eligibility file accessible by the one or more service provider computers, (2) the intervention service is contracted for by a claims processor computer identified by the destination identifier based upon a review of claims processor eligibility information from a eligible claims processor file accessible by the one or more service provider computers and (3) the pharmacy that provided the healthcare claim transaction has contracted to receive intervention service notifications based upon a review of pharmacy eligibility information from a pharmacy eligibility file accessible by the one or more service provider computers, wherein the intervention service comprises at least one of wellness screening, blood pressure monitoring, medication therapy management services, immunization messaging, cash prescription monitoring, refill adherence, high-risk medication monitoring or diabetic screening or monitoring;
   in an instance in which a determination is made that the intervention service is available for the patient, the intervention service is contracted for by the claims processor computer and the pharmacy has contracted to receive intervention service notifications, identifying, by the one or more service provider computers from an intervention parameter file and based at least in part on the destination identifier, a plurality of screening parameters for the intervention service available to the patient identified by the patient identifier;
   wherein for each of the plurality of screening parameters, the method further comprises:
   a. identifying, by the one or more service provider computers, a first screening parameter of the plurality of screening parameters for the intervention service, wherein the first screening parameter is identified by a counter variable that is set equal to 1;
   b. identifying, by the one or more service provider computers, at least one of a reject code or a reject message providing a notification of the first screening parameter;
   c. generating, by the one or more service provider computers, a reject response to the healthcare claim transaction;
   d. inserting, by the one or more service provider computers, the identified at least one reject code or reject message providing a notification of the first screening parameter for the intervention service into the reject response to the healthcare claim transaction;
   e. transmitting, by the one or more service provider computers, the reject response to the healthcare claim transaction to the pharmacy computer, wherein the reject response to the healthcare claim transaction is transmitted prior to adjudication of the healthcare claim transaction by a claims processor computer and includes an indication that the healthcare claim transaction should be resubmitted;
   f. receiving, by the one or more service provider computers, a resubmitted healthcare claim transaction from the pharmacy computer, the resubmitted healthcare claim transaction comprising a pharmacy identifier identifying the pharmacy associated with the pharmacy computer, the patient identifier for the patient, and the destination identifier;
   g. determining, by the one or more service provider computers, if the resubmitted healthcare claim transaction includes a first patient parameter data for the first screening parameter for the intervention service;
   h. identifying, by the one or more service provider computers and based at least on the positive determination that the resubmitted healthcare claim transaction includes the first patient parameter data for the first screening parameter, the first patient parameter data for the first screening parameter; and
   i. repeating, by the one or more service provider computers, steps (a)-(h) for each of the plurality of screening parameters for the intervention service to receive a plurality of patient parameter data corresponding to the plurality of screening parameters for the intervention service, wherein repeating steps (a)-(h) comprises evaluating, by the one or more service provider computers and based at least in part on the destination identifier of the resubmitted healthcare claim transaction identifying the intervention service to be provided, the plurality of screening parameters from the intervention parameter file that are to be requested; and in an instance in which at least one screening parameter remains to be requested, incrementing the counter variable that designates the screening parameter to be requested prior to repeating steps (a)-(h); and transmitting, by the one or more service provider computers, the received plurality of patient parameter data for the intervention service to the claims processor computer associated with a claims processor, wherein transmitting comprises routing the plurality of patient parameter data for the intervention service to the claims processor computer in accordance with a routing table associated with the one or more service provider computers.

2. The computer-implemented method of claim 1, further comprising:

receiving, by the one or more service provider computers from the pharmacy computer, a prior healthcare claim transaction comprising a product identifier for a prescribed product and a patient identifier identifying a patient to receive the prescribed product, wherein the prior healthcare transaction is received by the one or more service provider computers prior to the healthcare claim transaction;

determining, by the one or more service provider computers and based at least in part on the patient identifier, at least one intervention service available for the patient identified in the prior healthcare claim transaction;

generating, by the one or more service provider computers, a prior reject response to the prior healthcare claim transaction, wherein the prior reject response comprises an indicator of the intervention service available for the patient; and transmitting, by the one or more service provider computers, the prior reject response to the pharmacy computer.

3. The computer-implemented method of claim 1, wherein identifying the plurality of screening parameters for the intervention service comprises:

comparing, by the one or more service provider computers, the destination identifier to at least one intervention service destination identifier that identifies at least one intervention service to determine if a match exists;

determining, by the one or more service provider computers and based at least in part on the comparison of the destination identifier to the at least one intervention service destination identifier, that the healthcare claim transaction is for the intervention service available to the patient; and identifying, by the one or more service provider computers and based at least in part on the determination that the healthcare claim transaction is for the intervention service available to the patient, the plurality of screening parameters for data to obtain from the patient in the intervention service.

4. The computer-implemented method of claim 1, further comprising:

f. 1. determining, by the one or more service provider computers and based at least in part on the pharmacy identifier and the patient identifier, that the pharmacy is conducting the intervention service for the patient.

5. The computer-implemented method of claim 1, further comprising:

g. 1. parsing, by the one or more service provider computers and based at least on the negative determination that the resubmitted healthcare claim transaction includes the first patient parameter data for the first screening parameter, the resubmitted healthcare claim transaction to identify a reason code, wherein the reason code designates a reason that the first patient parameter data was not included in the resubmitted healthcare claim transaction;

g.2 storing, by the one or more service provider computers, the identified reason code; and g.3 modifying, by the one or more service provider computers, the resubmitted healthcare claim transaction by removing the identified reason code from the resubmitted healthcare claim transaction.

6. The computer-implemented method of claim 5, further comprising:

g.4. transmitting the modified resubmitted healthcare claim transaction to a second claims processor computer for adjudication.

7. The computer-implemented method of claim 1, wherein the intervention service is a wellness screening intervention service for the patient and wherein the plurality of screening parameters for the wellness screening intervention service comprise at least two or more of: patient blood pressure, patient total cholesterol measurement, patient high-density lipoproteins cholesterol measurement, patient low-density lipoproteins cholesterol measurement, patient triglycerides measurement, patient blood glucose measurement, patient height, patient weight, and patient waist measurement.

8. The computer-implemented method of claim 1, wherein transmitting the received plurality of patient parameter data for the intervention service to a claims processor computer comprises:

generating, by the one or more service provider computers, a single healthcare claim transaction;

inserting, by the one or more service provider computers, each of the plurality of patient parameter data into the single healthcare claim transaction; and transmitting, by the one or more service provider computers, the single healthcare claim transaction to the claims processor computer.

9. A system for determining patient intervention services, the system comprising:

at least one memory operable to store computer-executable instructions; and at least one processor configured to access the at least one memory and execute the computer-executable instructions to:

receive, from a pharmacy computer associated with a pharmacy, a healthcare claim transaction comprising a patient identifier identifying a patient and a destination identifier;

in response to receipt of the healthcare claim transaction, determine whether (1) an intervention service is available for the patient identified by the patient identifier based upon a review of patient eligibility information from a patient eligibility file accessible by the system, (2) the intervention service is contracted for by a claims processor computer identified by the destination identifier based upon a review of claims processor eligibility information from a eligible claims processor file accessible by the one or more service provider computers and (3) the pharmacy that provided the healthcare claim transaction has contracted to receive intervention service notifications based upon a review of pharmacy eligibility information from a pharmacy eligibility file accessible by the one or more service provider computers, wherein the intervention service comprises at least one of wellness screening, blood pressure monitoring, medication therapy management services, immunization messaging, cash prescription monitoring, refill adherence, high-risk medication monitoring or diabetic screening or monitoring;

in an instance in which a determination is made that the intervention service is available for the patient, the intervention service is contracted for by the claims processor computer and the pharmacy has contracted to receive intervention service notifications, identify, from an intervention parameter file, screening parameters for the intervention service available to the patient identified by the patient identifier;

wherein for each of the plurality of screening parameters, the at least one processor is further configured to access the at least one memory and execute the computer-executable instructions to:

a. identify a first screening parameter of the plurality of screening parameters for the intervention service, wherein the first screening parameter is identified by a counter variable that is set equal to 1;

b. identify, based on the first screening parameter, at least one of a reject code or a reject message providing a notification of the first screening parameter;

c. generate a reject response to the healthcare claim transaction;

d. insert the identified at least one reject code or reject message providing a notification of the first screening parameter for the intervention service into the reject response to the healthcare claim transaction;

e. direct communication of the reject response to the healthcare claim transaction to the pharmacy computer, wherein the reject response to the healthcare claim transaction is communicated prior to adjudication of the healthcare claim transaction by a claims processor computer and includes an indication that the healthcare claim transaction should be resubmitted;

f. receive a resubmitted healthcare claim transaction from the pharmacy computer, the resubmitted healthcare claim transaction comprising a pharmacy identifier identifying the pharmacy associated with the pharmacy computer, the patient identifier for the patient, and the destination identifier;

g. determine if the resubmitted healthcare claim transaction includes a first patient parameter data for the first screening parameter for the intervention service;

h. identify, based at least on the positive determination that the resubmitted healthcare claim transaction includes the first patient parameter data for the first screening parameter, the first patient parameter data for the first screening parameter; and i. repeat steps (a)-(h) for each of the plurality of screening parameters for the intervention service to receive a plurality of patient parameter data corresponding to the plurality of screening parameters for the intervention service, wherein repeating steps (a)-(h) comprises evaluating, based at least in part on the destination identifier of the resubmitted healthcare claim transaction identifying the intervention service to be provided, the plurality of screening parameters from the intervention parameter file that are to be requested; and in an instance in which at least one screening parameter remains to be requested, incrementing the counter variable that designates the screening parameter to be requested prior to repeating steps (a)-(h); and direct communication of the received plurality of patient parameter data for the intervention service to the claims processor computer associated with a claims processor, wherein transmitting comprises routing the plurality of patient parameter data for the intervention service to the claims processor computer in accordance with a routing table associated with the system.

10. The system of claim 9, wherein the at least one processor is further configured to access the at least one memory and execute the computer-executable instructions to:

receive, from the pharmacy computer, a prior healthcare claim transaction comprising a product identifier for a prescribed product and the patient identifier identifying the patient to receive the prescribed product, wherein the prior healthcare transaction is received by the one or more service provider computers prior to the healthcare claim transaction;

determine, based at least in part on the patient identifier, at least one intervention service available for the patient identified in the prior healthcare claim transaction;

generate a prior reject response to the prior healthcare claim transaction, wherein the prior reject response comprises an indicator of the intervention service available for the patient; and direct communication of the prior reject response to the pharmacy computer.

11. The system of claim 9, wherein the at least one processor is configured to identify the plurality of screening parameters for the intervention service by accessing the at least one memory and executing the computer-executable instructions to:

compare the destination identifier to at least one intervention service destination identifier that identifies at least one intervention service to determine if a match exists;

determine, based at least in part on the comparison of the destination identifier to the at least one intervention service destination identifier, that the healthcare claim transaction is for the intervention service available to the patient; and identify, based at least in part on the determination that the healthcare claim transaction is for the intervention service available to the patient, the plurality of screening parameters for data to obtain from the patient in the intervention service.

12. The system of claim 9, wherein the at least one processor is further configured to access the at least one memory and execute the computer-executable instructions to:

f. 1. determine, based at least in part on the pharmacy identifier and the patient identifier, that the pharmacy is conducting the intervention service for the patient.

13. The system of claim 9, wherein the at least one processor is further configured to access the at least one memory and execute the computer-executable instructions to:

g. 1. parse, based at least on the negative determination that the resubmitted healthcare claim transaction includes the first patient parameter data for the first screening parameter, the resubmitted healthcare claim transaction to identify a reason code, wherein the reason code designates a reason that the first patient parameter data was not included in the resubmitted healthcare claim transaction;

g.2 store the identified reason code in the at least one memory; and g.3 modify the resubmitted healthcare claim transaction by removing the identified reason code from the resubmitted healthcare claim transaction.

14. The system of claim 13, wherein the at least one processor is further configured to access the at least one memory and execute the computer-executable instructions to:

g.4. direct communication of the modified resubmitted healthcare claim transaction to a second claims processor computer for adjudication.

15. The system of claim 9, wherein the intervention service is a wellness screening intervention service for the patient and wherein the plurality of screening parameters for the wellness screening intervention service comprise at least two or more of: patient blood pressure, patient total cholesterol measurement, patient high-density lipoproteins cholesterol measurement, patient low-density lipoproteins cholesterol measurement, patient triglycerides measurement, patient blood glucose measurement, patient height, patient weight, and patient waist measurement.

16. The system of claim 9, wherein the at least one processor is configured to direct communication of the received plurality of patient parameter data for the intervention service to the claims processor computer by accessing the at least one memory and executing the computer-executable instructions to:

generate a single healthcare claim transaction;

insert each of the plurality of patient parameter data into the single healthcare claim transaction; and direct communication of the single healthcare claim transaction to the claims processor computer.

17. A computer-implemented method for determining patient intervention services, the method comprising:

receiving, by one or more service provider computers comprising one or more processors from a pharmacy computer associated with a pharmacy, a healthcare claim transaction comprising first data comprising a first prescription number, a first fill number, a first pharmacy identifier, a first date of service, a first product identifier for a prescribed product, a first patient identifier identifying a patient to receive the prescribed product and a destination identifier;

in response to receipt of the healthcare claim transaction, determining, by the one or more service provider computers, whether (1) at least one intervention service is available for the patient identified by the first patient identifier in the healthcare claim transaction based upon a review of patient eligibility information from a patient eligibility file accessible by the one or more service provider computers, (2) the intervention service is contracted for by a claims processor computer identified by the destination identifier based upon a review of claims processor eligibility information from a eligible claims processor file accessible by the one or more service provider computers and (3) the pharmacy that provided the healthcare claim transaction has contracted to receive intervention service notifications based upon a review of pharmacy eligibility information from a pharmacy eligibility file accessible by the one or more service provider computers, wherein the intervention service available for the patient comprises at least one of wellness screening, blood pressure monitoring, medication therapy management services, immunization messaging, cash prescription monitoring, refill adherence, high-risk medication monitoring or diabetic screening or monitoring;

in an instance in which a determination is made that the intervention service is available for the patient, the intervention service is contracted for by the claims processor computer and the pharmacy has contracted to receive intervention service notifications, generating, by the one or more service provider computers, a reject response to the healthcare claim transaction, wherein the reject response comprises an indicator of the intervention service available for the patient, and wherein an intervention parameter file identifies a plurality of screening parameters for the intervention service;

transmitting, by the one or more service provider computers, the reject response to the pharmacy computer, wherein the reject response to the healthcare claim transaction is transmitted prior to adjudication of the healthcare claim transaction by the claims processor computer and includes an indication that the healthcare claim transaction should be resubmitted;

receiving, by the one or more service provider computers from the pharmacy computer, a resubmitted healthcare claim transaction comprising second data comprising a second prescription number, a second fill number, a second pharmacy identifier, a second date of service, and the patient identifier identifying the patient;

comparing, by the one or more service provider computers, at least a portion of the first data to at least a portion of the second data to determine if a match exists between the portion of the first data and the portion of the second data;

in an instance in which the healthcare claim transaction is for an intervention service available to the patient and in which the resubmitted healthcare claim transaction includes a screening parameter for the intervention service, repeating, by the one or more service provider computers, the steps of generating the reject response, transmitting the reject response, receiving another resubmitted healthcare claim transaction including other data and another screening parameter for the intervention service and comparing at least a portion of the first data to a least a portion of the other data to determine if a match exists, wherein repeating the steps comprises evaluating, by the one or more service provider computers, the plurality of screening parameters from the intervention parameter file that are to be requested; and in an instance in which at least one screening parameter remains to be requested, incrementing a counter variable that designates the screening parameter to be requested prior to repeating the steps;

otherwise, determining, by the one or more service provider computers and based at least in part on the comparison, that the healthcare claim transaction is not for an intervention service available to the patient;

parsing, by the one or more service provider computers and based at least on the determination that the resubmitted healthcare claim transaction is not for an intervention service available to the patient, the resubmitted healthcare claim transaction to identify a reason code, wherein the reason code designates a reason that the intervention service available to the patient was not completed;

storing, by the one or more service provider computers, the identified reason code;

modifying, by the one or more service provider computers, the resubmitted healthcare claim transaction by removing the identified reason code from the resubmitted healthcare claim transaction; and transmitting, by the one or more service provider computers, the modified resubmitted healthcare claim transaction to the claims processor computer that is identified by the destination identifier and that is associated with a claims processor for adjudication, wherein transmitting comprises routing the modified resubmitted healthcare claim transaction to the claims processor computer in accordance with a routing table associated with the one or more service provider computers.

18. The computer-implemented method of claim 17, further comprising:

receiving, by the one or more service provider computers, an adjudicated response to the modified resubmitted healthcare claim transaction; and transmitting, by the one or more service provider computers, the adjudicated response to the pharmacy computer.

19. A system for determining patient intervention services, the system comprising:

at least one memory operable to store computer-executable instructions; and at least one processor configured to access the at least one memory and execute the computer-executable instructions to:

receive, from a pharmacy computer associated with a pharmacy, a healthcare claim transaction comprising first data comprising a first prescription number, a first fill number, a first pharmacy identifier, a first date of service, a first product identifier for a prescribed product, a first patient identifier identifying a patient to receive the prescribed product and a destination identifier;

in response to receipt of the healthcare claim transaction, determine whether (1) at least one intervention service is available for the patient identified by the first patient identifier in the healthcare claim transaction based upon a review of patient eligibility information from a patient eligibility file accessible by the system, (2) the intervention service is contracted for by a claims processor computer identified by the destination identifier based upon a review of claims processor eligibility information from a eligible claims processor file accessible by the system and (3) the pharmacy that provided the healthcare claim transaction has contracted to receive intervention service notifications based upon a review of pharmacy eligibility information from a pharmacy eligibility file accessible by the system, wherein the intervention service available for the patient comprises at least one of wellness screening, blood pressure monitoring, medication therapy management services, immunization messaging, cash prescription monitoring, refill adherence, high-risk medication monitoring or diabetic screening or monitoring;

in an instance in which a determination is made that the intervention service is available for the patient, the intervention service is contracted for by the claims processor computer and the pharmacy has contracted to receive intervention service notifications, generate a reject response to the healthcare claim transaction, wherein the reject response comprises an indicator of the intervention service available for the patient, and wherein an intervention parameter file identifies a plurality of screening parameters for the intervention service;

direct communication of the reject response to the pharmacy computer, wherein the reject response to the healthcare claim transaction is transmitted prior to adjudication of the healthcare claim transaction by the claims processor computer and includes an indication that the healthcare claim transaction should be resubmitted;

receive, from the pharmacy computer and subsequent to the communication of the reject response, a resubmitted healthcare claim transaction comprising second data comprising a second prescription number, a second fill number, a second pharmacy identifier, a second date of service, and the patient identifier identifying the patient;

compare at least a portion of the first data to at least a portion of the second data to determine if a match exists between the portion of the first data and the portion of the second data;

in an instance in which the healthcare claim transaction is for an intervention service available to the patient and in which the resubmitted healthcare claim transaction includes a screening parameter for the intervention service, repeat the steps of generating the reject response, transmitting the reject response, receiving another resubmitted healthcare claim transaction including other data and another screening parameter for the intervention service and comparing at least a portion of the first data to a least a portion of the other data to determine if a match exists, wherein repeating the steps comprises evaluating the plurality of screening parameters from the intervention parameter file that are to be requested; and in an instance in which at least one screening parameter remains to be requested, incrementing a counter variable that designates the screening parameter to be requested prior to repeating the steps;

otherwise, determine, based at least in part on the comparison, that the healthcare claim transaction is not for an intervention service available to the patient;

parse, based at least on the determination that the resubmitted healthcare claim transaction is not for an intervention service available to the patient, the resubmitted healthcare claim transaction to identify a reason code, wherein the reason code designates a reason that the intervention service available to the patient was not completed;

store the identified reason code;

modify the resubmitted healthcare claim transaction by removing the identified reason code from the resubmitted healthcare claim transaction; and direct communication of the modified resubmitted healthcare claim transaction to the claims processor computer that is identified by the destination identifier and that is associated with a claims processor for adjudication, wherein the modified resubmitted healthcare claim transaction is transmitted by routing the modified resubmitted healthcare claim transaction to the claims processor computer in accordance with a routing table associated with the system.

20. The system of claim 19, wherein the at least one processor is further configured to access the at least one memory and execute the computer-executable instructions to:

receive an adjudicated response to the modified resubmitted healthcare claim transaction; and direct communication of the adjudicated response to the pharmacy computer.

\* \* \* \* \*